(12) United States Patent
Matsumura et al.

(10) Patent No.: US 8,277,382 B2
(45) Date of Patent: Oct. 2, 2012

(54) AUTOMATED PRESSING DEVICE AND ULTRASONIC DIAGNOSIS APPARATUS USING THE DEVICE

(75) Inventors: Takeshi Matsumura, Tokyo (JP);
Tsuyoshi Mitake, Tokyo (JP);
Tomoyuki Miyazawa, Yokohama (JP)

(73) Assignee: Hitachi Medical Corporation, Tokyo (JP)

(*) Notice: Subject to any disclaimer, the term of this patent is extended or adjusted under 35 U.S.C. 154(b) by 994 days.

(21) Appl. No.: 12/224,600

(22) PCT Filed: Mar. 2, 2007

(86) PCT No.: PCT/JP2007/054096
§ 371 (c)(1),
(2), (4) Date: Nov. 12, 2008

(87) PCT Pub. No.: WO2007/100107
PCT Pub. Date: Sep. 7, 2007

(65) Prior Publication Data
US 2009/0306515 A1 Dec. 10, 2009

(30) Foreign Application Priority Data
Mar. 2, 2006 (JP) .................. 2006-056050

(51) Int. Cl.
*A61B 8/14* (2006.01)
(52) U.S. Cl. .......... 600/459; 600/438; 600/443
(58) Field of Classification Search .......... 600/437, 600/438, 443, 446, 459
See application file for complete search history.

(56) References Cited

U.S. PATENT DOCUMENTS

| | | | |
|---|---|---|---|
| 7,914,456 B2* | 3/2011 | Osaka et al. | 600/447 |
| 2004/0254460 A1 | 12/2004 | Burcher et al. | |
| 2005/0085728 A1 | 4/2005 | Fukuda | |
| 2009/0018444 A1* | 1/2009 | Osaka et al. | 600/437 |
| 2009/0177083 A1* | 7/2009 | Matsumura | 600/437 |
| 2010/0016724 A1* | 1/2010 | Arai et al. | 600/443 |

FOREIGN PATENT DOCUMENTS

| | | |
|---|---|---|
| DE | 199 36 554 A1 | 2/2001 |
| EP | 1 629 777 A1 | 3/2006 |
| JP | 2005-013283 | 1/2005 |
| JP | 2005-144155 | 6/2005 |
| WO | WO 03/022152 A1 | 3/2003 |
| WO | WO 2004/105615 A1 | 12/2004 |

* cited by examiner

*Primary Examiner* — Brian Casler
*Assistant Examiner* — Amanda Lauritzen
(74) *Attorney, Agent, or Firm* — Antonelli, Terry, Stout & Kraus, LLP

(57) ABSTRACT

An automated pressing device (3) for an ultrasonic diagnosis apparatus according to the present invention is constituted by being provided with a probe holding member (21) including an attaching portion (31) to which a probe (2) is detachably attached and a griping portion (32) to which the attaching portion is slidably attached together with the probe attached thereto so as to permit advancing and retreating of an ultrasonic transmission and reception plane (27) of the probe, a motive power transmission wire (23) including a flexible cylindrical body (41) of which one end is secured to the griping portion in the probe holding member and an inner wire (42) that is inserted in the cylindrical body and of which one end is coupled to the attaching portion and a pressing motive power means (24) to which the other end of the cylindrical body in the motive power transmission wire is secured and that couples with the other end of the inner wire to advance and retreat the same. Thereby, a user friendly automated pressing device is realized that permits to eliminate influences of electromagnetic noises as well as permits to apply a stable pressing to a body surface of a subject via such as a motor and a spring.

17 Claims, 15 Drawing Sheets

FIG. 3
(A)
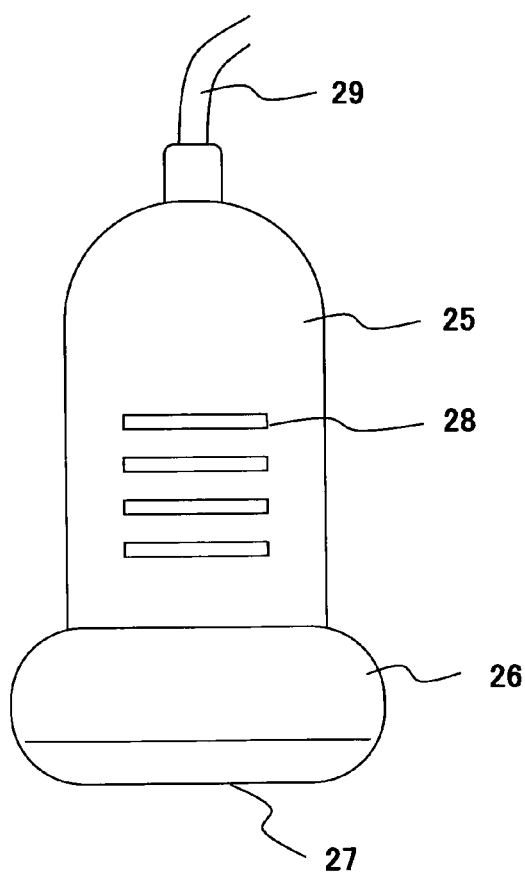
(B)
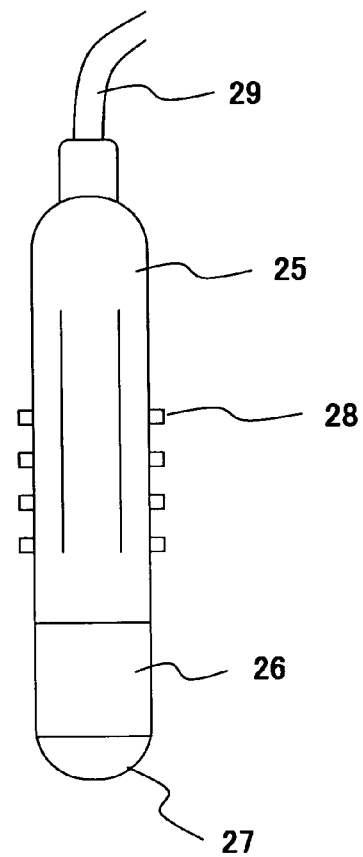

AUTOMATED PRESSING DEVICE AND ULTRASONIC DIAGNOSIS APPARATUS USING THE DEVICE

FIELD OF THE INVENTION

The present invention relates to an automated pressing device for a subject used for obtaining elasticity information of the subject at the time of ultrasonic diagnosis and an ultrasonic diagnosis apparatus using the device.

CONVENTIONAL ART

In ultrasonic diagnosis, while pressing (pressure application, pressure reduction) a biological tissue of a subject, elasticity information caused thereby in the tissue such as displacement, distortion or modulus of elasticity based thereon are computed, and these elasticity information is visualized and displayed as an elasticity image for serving diagnosis of, for example, benignancy and malignancy of a tumor in the tissue.

Since the elasticity information of a biological tissue obtained by pressing the same varies depending on manners of pressing due to non-linearity of the biological tissue with respect to pressing, in order to obtain a stable elasticity image meeting objective evaluation, it is necessary to adjust pressing conditions such as strength of pressing applied to a probe, velocity of pressing and repetition cycle of pressing in predetermined ranges, which requires experienced skill. Therefore, it has been proposed to automate a mechanism that presses a biological tissue via a probe.

For example, in an automatic pressing device disclosed in JP-A-2005-13283 (patent document 1), a probe is attached in a grip portion in such a manner that an ultrasonic transmission and reception plane of transducers in the probe is able to advance and retreat in the axial direction of the grip portion, and the ultrasonic transducers are caused to advance and retreat by a motor accommodated in the grip portion via a rack and pinion so as to press a subject. With the disclosed device, through control of the motor the pressing conditions applied to the biological tissue via the ultrasonic transmission and reception plane can be kept in predetermined ranges.

However, according to the conventional art disclosed in patent document 1, since the motor is accommodated inside a casing of the probe grip portion, the size of the probe itself enlarges and the weight thereof increases, thereby, there arises a problem that the manipulating operation thereof during diagnosis is difficult. Further, due to electromagnetic waves generated from the motor or from control signals to the motor, when noises are superposed on received signals of the transducers, an adverse effect is likely caused on quality of the image. Still further, since an inspector and a subject are placed in an environment close to the motor, a design is required that fully takes into account of safety with respect to a high voltage applied to the motor.

The document further discloses to constitute a drive system such as the motor as a unit form and to load the same at the outside of the probe, however, such can not avoid to substantially enlarge the size of the probe itself and to increase the weight thereof. Further, the adverse effect due to the electromagnetic waves generated from such as the motor also cannot be avoided.

Further, in place of the drive system using the motor and the rack and pinion, when a drive system using a hydraulic cylinder and a pump that is also disclosed is employed, the problems relating to the motor type can be resolved. However, since the hydraulic cylinder has to be attached at the probe grip portion and to be connected to the pump via a pipe, there arise problems that a possible oil leakage is feared as well as its handling is hard and the manipulating operation thereof during diagnosis is difficult.

Still further, if a drive system using a pneumatic cylinder and a pneumatic pump is employed, the problems in connection with the motor type and the hydraulic pump type are resolved. However, since the pneumatic cylinder has to be attached at the probe grip portion as well as to be connected to the pump via a pipe, a delay of motive power transmission due to contraction or expansion of the pneumatic pipe where air of compressive fluid flows cannot be neglected. For this reason, it is difficult such as to realize a pressing motion having amplitude, for example, about 0.5 mm and to obtain a sufficient pressing force.

SUMMARY OF THE INVENTION

Task to be Solved by the Invention

A task of the present invention is to realize a user friendly automated pressing device with a detachable probe.

Measure for Solving the Task

In order to solve the above task, a first aspect of an automated pressing device according to the present invention is constituted by being provided with a probe holding member including an attaching portion to which a probe is detachably attached and a griping portion to which the attaching portion is attached together with the probe attached thereto so as to permit advancing and retreating in ultrasonic transmission and reception direction of the probe, a motive power transmission means including a cylindrical body of which one end is secured to the griping portion of the probe holding member and a coupling member that is inserted in the cylindrical body and of which one end is coupled to the attaching portion and a pressing motive power means to which the other end of the cylindrical body in the motive power transmission means is secured and that causes the other end of the coupling member to advance and retreat.

Namely, according to the first aspect of the present invention, when the advancing and retreating of the coupling member is repeated via the pressing motive power means, the attaching portion coupled to the coupling member is advanced and retreated with respect to the griping portion. Thereby, the probe attached to the attaching portion is advanced and retreated with respect to the griping portion in the ultrasonic transmission and reception direction. Therefore, when an inspector contacts the probe to a subject while firmly holding the griping portion, the probe advances and retreats toward the subject so as to repeatedly apply pressing to the subject.

In particular, since the pressing motive power means that drives the probe to advance and retreat and the probe holding member are provided separately, and the both are coupled via the motive power transmission means, the size enlargement of the probe and the probe holding member which are gripped and manipulated by a hand is prevented, the weight thereof is lightened and the user friendliness is enhanced. Further, since the pressing motive power means can be located remote from the probe, the possible influences of the electromagnetic wave noises to the ultrasonic reception noises can be eliminated, even if a motor having excellent controllability is used for the pressing motive power means. Further, a possible electric shock from a power source feeding the motor can be avoided.

Further, according to the first aspect of the present invention, since the drive force for advancing and retreating the probe is transmitted via the coupling member of the motive power transmission means, the coupling member is required to have a strength and rigidity capable of transmitting forces in both pushing and pulling directions.

However, in the automated pressing device according to the present invention, the coupling member can be realized by a motive power transmission wire using an inner wire with no strength and rigidity in pushing direction. Namely, a second aspect of an automated pressing device according to the present invention is to provide in the first aspect automated pressing device with an elastic member that energizes in a moving away direction the attaching portion with respect to the griping portion. According to the second aspect, by loosing the pulling force of the inner wire the probe advances through expansion of the elastic member to permit pressing of the subject. Further, by strengthening the pulling force of the inner wire the elastic member is compressed to retreat the probe and to weaken the pressing. Further, the present measure can be applied to the motive power transmission wire using a rigid inner wire capable of transmitting forces in pushing and pulling directions. In particular, according to the second aspect of the present invention, since the pressing force to the subject is determined by the elastic member, the maximum value of the pressing force can be kept constant.

Further, according to the first and second aspects of the present invention, the probe is detachably attached to the probe holding member, however, the present invention is not limited to such structure and the function of the probe holding member can be assembled integrally to the probe. Namely, a third aspect of an automated pressing device according to the present invention is constituted by being provided with a casing forming a griping portion for a probe, slide rails formed on the inner faces of the casing, a sliding member accommodated in the casing in a manner to be slidable along the slide rails, a transducer portion secured to the sliding member while projecting the ultrasonic transmission and reception plane of the probe from the casing, an elastic member that energizes the transducer portion in the direction of advancing from the casing along the slide rails, a motive power transmission wire including a flexible cylindrical body of which one end is secured to the casing and an inner wire that is inserted in the cylindrical body and of which one end is coupled to the sliding member and a pressing motive power means to which the other end of the cylindrical body of the motive power transmission wire is secured and that couples to the other end of the inner wire to advance and retreat the same. Thereby, according to the third aspect of the present invention, a probe having the automated pressing function can be realized in small size and lightweight.

Further, in place of pressing by advancing and retreating the inner wire of the motive power transmission wire as in the first through third aspects of the present invention, the probe can be advanced and retreated by transmitting rotating force via an inner wire. Namely, a fourth aspect of an automated pressing device according to the present invention is constituted by being provided with a probe holding member including an attaching portion to which a probe is detachably attached, a griping portion to which the attaching portion together with the probe attached thereto is slidably attached so as to permit advancing and retreating in ultrasonic transmission and reception direction of the probe and a screw screwed in the attaching portion along the direction of moving the griping portion toward or away from the attaching portion, a motive power transmission wire including a flexible cylindrical body one end of which is secured to the griping portion of the probe holding member and an inner wire that is inserted through the cylindrical body and one end of which is coupled to the screw and a drive means which is secured to the other end of the cylindrical body of the motive power transmission wire and couples to the other end of the inner wire to rotatably drive the inner wire.

According to the fourth aspect of the present invention, since no motive power due to the advancing and retreating of the inner wire is transmitted, transmission of vibration due to the advancing and retreating motion of the inner wire can be avoided, thereby, problems such as shifting in back and forth of the measurement cross section with reference to the probe are effectively avoided.

Advantages of the Invention

According to the present invention, a user friendly automated pressing device with a detachable probe can be realized. Further, according to the present invention, a user friendly automated pressing device is realized that permits to eliminate influences of electromagnetic wave noises to ultrasonic reception signals as well as permits to apply a stable pressing to the subject. Still further, according to the present invention, an automated pressing device is realized in which the weight of the probe portion is lightened to ease the manipulation thereof and that permits to effect a stable pressing.

BRIEF DESCRIPTION OF THE DRAWINGS

FIG. 3 is an outlook of an exemplary probe that is applicable to the embodiment 1.

BEST MODES FOR CARRYING OUT THE INVENTION

Herein below the present invention will be explained with reference to embodiments.

Embodiment 1

Figure 1:
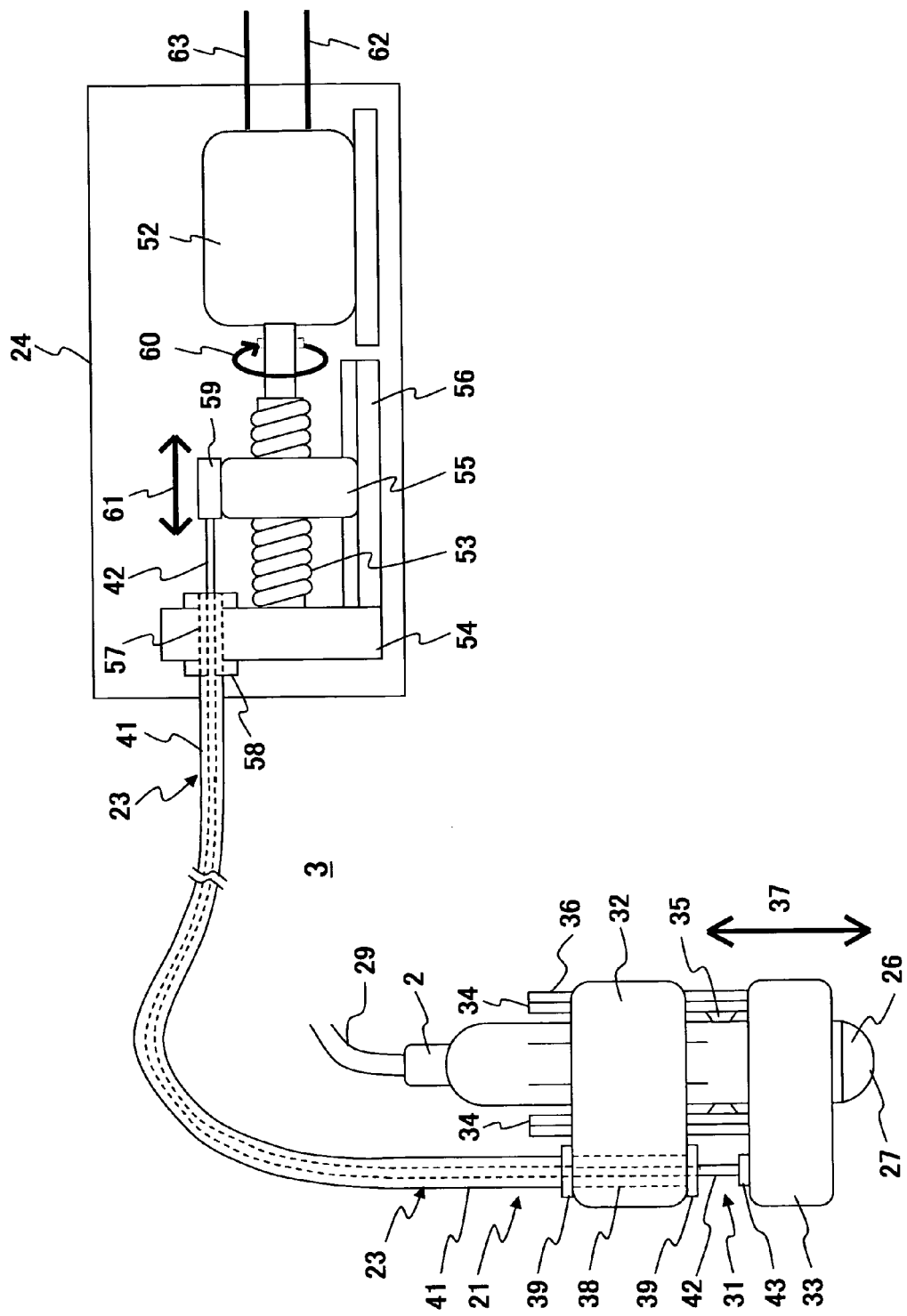
FIG. 1 is a constitutional diagram of an automated pressing device representing an embodiment 1 according to the present invention.
Figure 2:
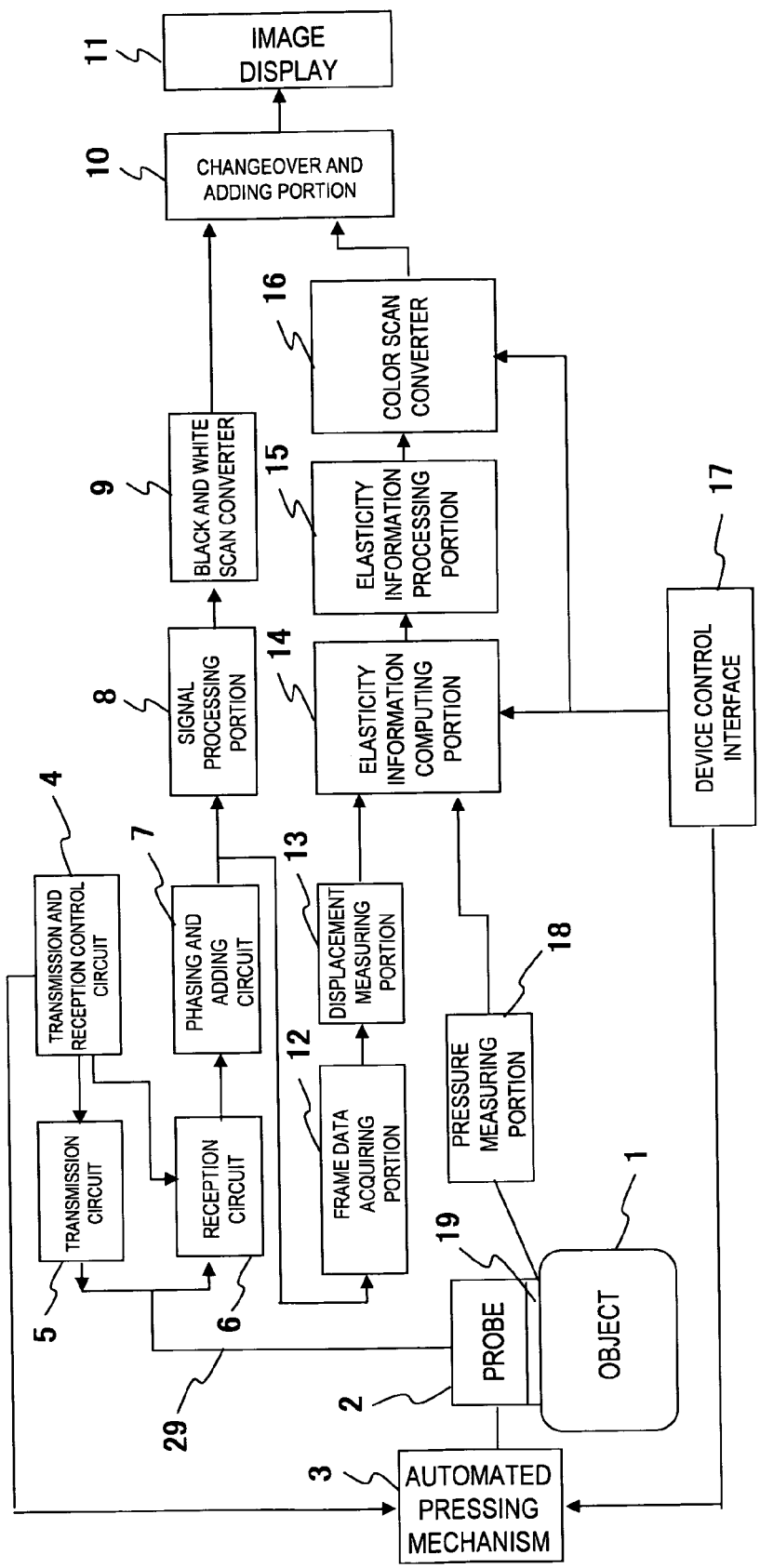
FIG. 2 is an entire constitutional diagram of an ultrasonic diagnosis apparatus using the automated pressing device of the embodiment 1.
Figure 4:
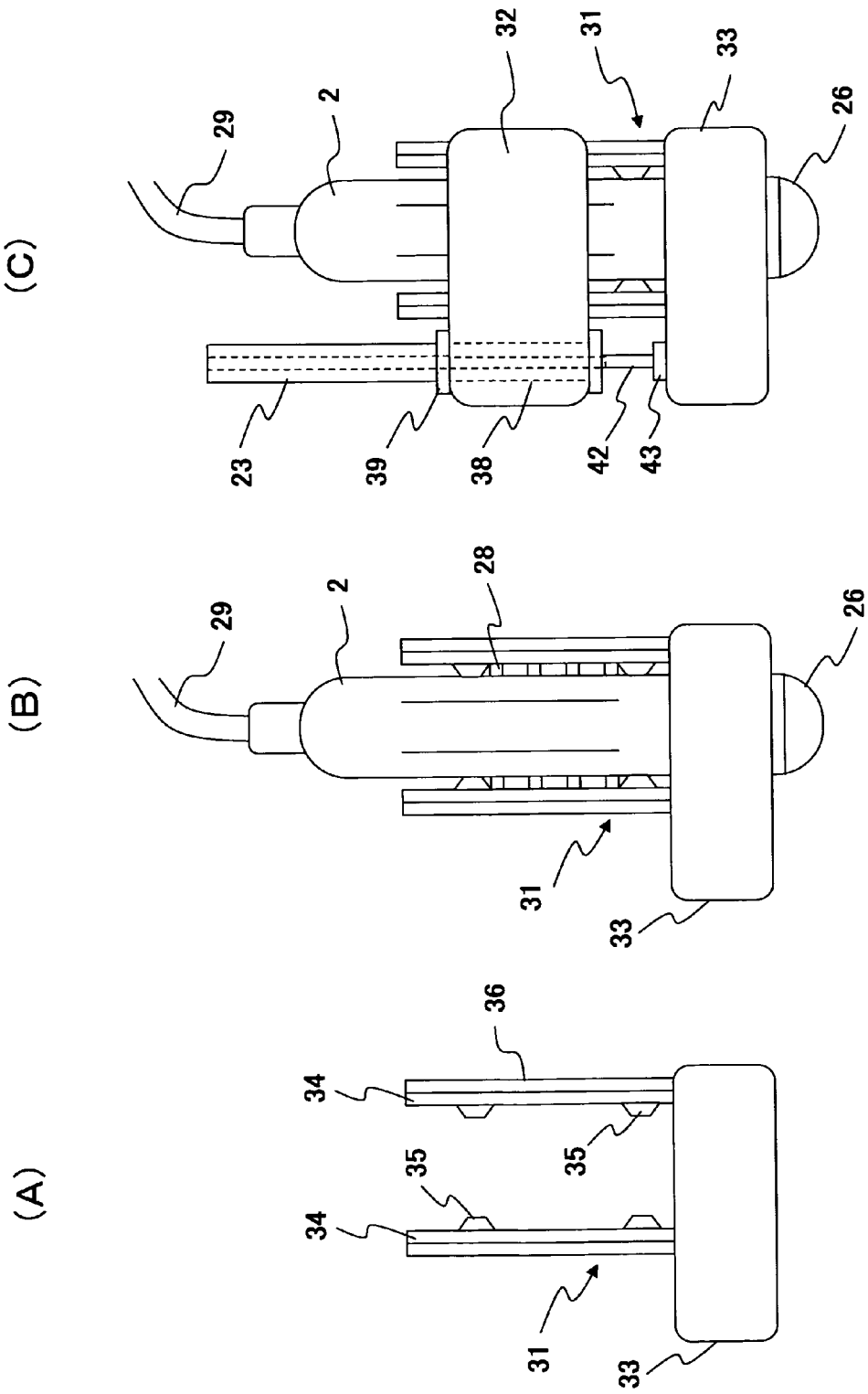
FIG. 4 is a diagram for explaining assembling steps of constitutional parts of the embodiment 1.
Figure 5:
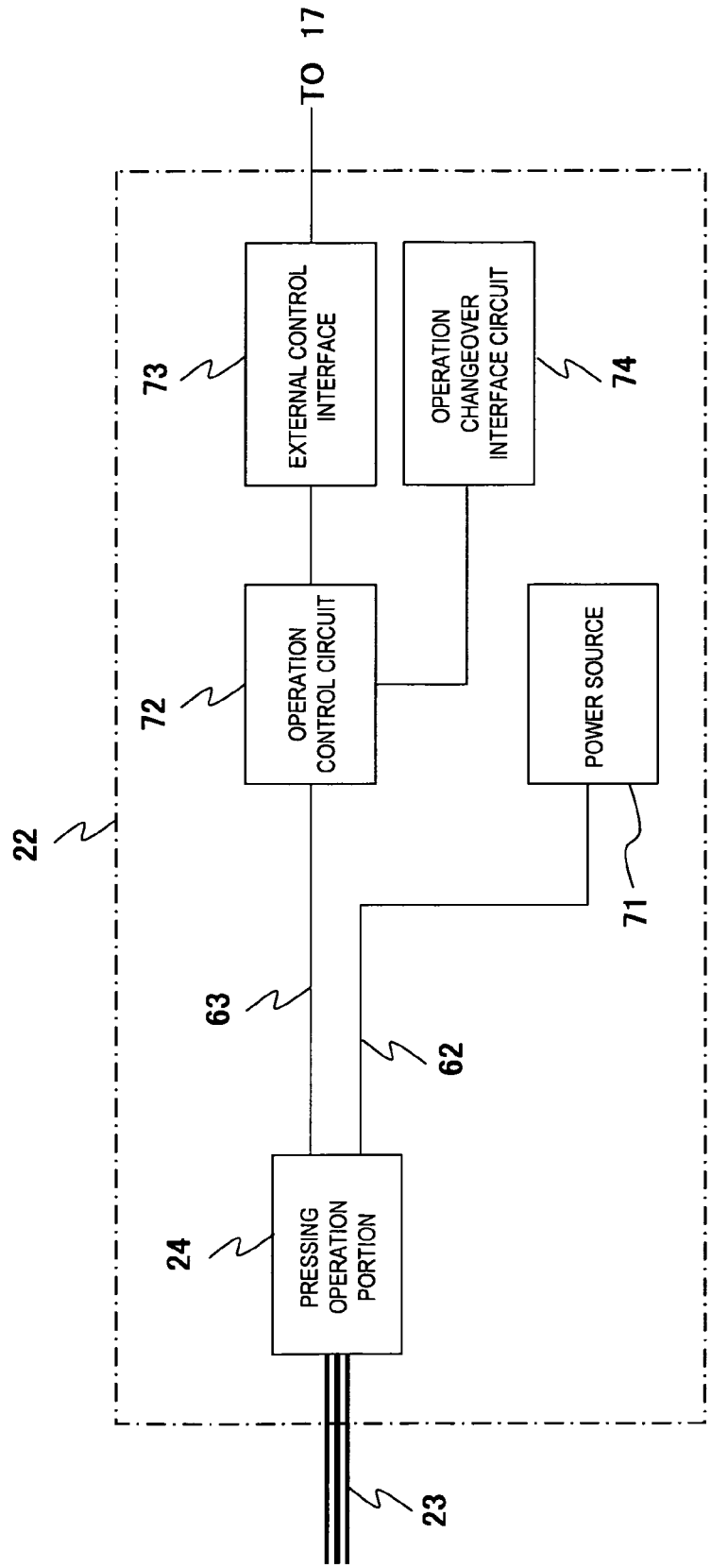
FIG. 5 is a block diagram of a pressing drive control unit in the automated pressing device of the embodiment 1.

FIG. 1 shows a constitutional diagram of an automated pressing device representing an embodiment according to the present invention. FIG. 2 shows an entire constitutional diagram of an ultrasonic diagnosis apparatus using the automated pressing device of the present embodiment. FIG. 3 shows an outlook of an exemplary probe that is applicable to the present embodiment. FIG. 4 shows a diagram for explaining assembling steps of constitutional parts of the present embodiment. FIG. 5 shows a block diagram of a pressing drive control unit in the automated pressing device of the present embodiment.

As shown in FIG. 2, an ultrasonic probe 2 is formed so as to include an ultrasonic transmission and reception plane arranged of a plurality of transducers for transmitting and receiving ultrasonics between a subject and the probe 2. The probe 2 is used by loading the same to an automated pressing device embodying features of the present invention and is permitted to automatically press the subject 1. The probe 2 is driven by ultrasonic pulses output from a transmission circuit 5 that is controlled by a transmission and reception control circuit 3, irradiates ultrasonic beams toward a focal point to be set within the subject 1 as well as scans the ultrasonic beams. Further, reflection echo signals received by the probe 2 are electronically scanned in the arrangement direction of the transducers, received by a reception circuit 6 that is controlled by the transmission and reception circuit 4 and subjected to signal reception processing such as amplification. The reflection echo signals subjected to the signal reception processing by the reception circuit 6 are subjected to phasing and adding of the plurality of reflection echo signals received by the plurality of transducers and added in a phasing and adding circuit 7.

A signal processing unit 8 performs signal processing such as gain correction, log compacting, demodulation, contour emphasizing and filtering for the reflection echo signals output from the phasing and adding circuit 7 and outputs the same to a black and white scan converter 9. The black and white scan converter 9 converts the reflection echo signals to digital signals and further converts into a two dimensional tomographic image (B mode image) data corresponding to a scanning plane of the ultrasonic beams. The tomographic image data output from the black and white scan converter 9 are displayed as a B mode image on a image display 11 via a change over and adding unit 10.

On the other hand, the reflection echo signals output from the phasing and adding circuit 7 are also introduced to a frame data acquiring portion 12 wherein a group of the reflection echo signals corresponding to the scanning plane (tomographic plane) of the ultrasonic beams are acquired by a component corresponding to a plurality of frames as frame data and are stored such as in a memory. A displacement measuring portion 13 sequentially takes frame data of a plurality of pairs having different acquiring moment stored in the frame data acquiring portion 12, subjects a pair of taken frame data to one or two dimensional correlating processing and determines displacement vectors at respective measuring points on the scanning plane to produce displacement frame data.

An elasticity information computing portion 14 is constituted by being provided with a distortion computing portion that determines distortion frame data of a biological tissue at respective measuring points based on the displacement frame data and an elastic module computing portion that determines elastic modules of the biological tissue at respective measuring points based on the distortion frame data to produce elastic module frame data. When determining the elastic modules, the elasticity information computing portion 14 takes values of pressure measured by a pressure measurement portion 18 and computes stresses at the respective points based on the taken values to determine elastic modules of the biological tissue from the computed stresses and the distortion. The pressure measurement portion 18 computes stresses at the measurement points inside the subject 1 based on pressure detected by pressure sensors 19 disposed between the ultrasonics transmission and reception plane of the probe 2 and the subject 1.

Now, the detail structure of the automated pressing device 3 representing a feature of the present embodiment will be explained with reference to FIG. 1. As shown in the drawing, the automated pressing device 3 of the present embodiment is constituted by including a probe holding member 21 to which the probe 2 is detachably attached, a pressing motive power portion 24 constituting a pressing drive control portion 22 (illustrated in FIG. 5) and a motive power transmission wire 23 coupling the probe holding member 21 and the pressing motive power portion 24. The probe 2 of the present embodiment is formed by including a casing 25 formed in a shape of flat container and a transducer portion 26 provided at the bottom end of the casing 25 in the drawing as shown in the front view in FIG. 3 (A) and the side view in FIG. 3 (B). The bottom plane in the drawing of the transducer portion 26 constitutes an ultrasonics transmission and reception plane 27. On the front and rear faces of the casing 25 a plurality of protuberances 28 are provided which are used for preventing slipping when the probe 2 is gripped by a hand. Further from the top of the casing a cable 29 is led out so as to permit connection with the transmission circuit 5 and the reception circuit 6 as shown in FIG. 1.

As shown in FIG. 1, the probe holding member 21 is formed by including an attaching portion 31 to which the probe 2 is detachably attached and a gripping portion 32 to which the attaching portion 31 is slidably attached. The attaching portion 31 is formed by including a stage portion 33 in a flat plate and a pair of catching members 34 provided while standing up from the upper face of the stage portion 33 and facing each other as shown in FIG. 4 (A). The two catching members 34 are for holding the casing 25 of the probe 2 by catching as shown in FIG. 4 (B) and on the opposing inner faces a plurality of protuberances 35 are formed for engaging with the plurality of the protuberances 28 of the casing 25. Although not illustrated in the drawing, at a portion in the stage portion 33 between the pair of the catching members 34, a through hole is provided which permits insertion of the probe 2. When the probe 2 is passed through the through hole and attached in the attaching portion 31, the ultrasonics transmission and reception plane 27 of the transducer portion 26 is designed to protrude by a predetermined amount from the bottom plane of the stage portion 33. Further, on the outer faces of the pair of catching members 34 slide rails 36 are respectively formed.

On the other hand, the gripping portion 32 is provided with a hole that permits insertion of the probe 2 under a condition that the probe 2 is attached between the pair of catching members 34, and on the inner face of the hole grooves are formed for permitting sliding of the slide rails 36 of the attaching portion 31. Thereby, the probe 2 is disposed in a manner that the ultrasonics transmission and reception plane 27 is permitted to advance and retreat in the sliding direction of the attaching portion 31 (in an arrow 37 in FIG. 1). Further, in order to prevent a hand of an inspector from touching to such as slide rails 36 of the attaching portion 31 inside the gripping portion 32 when the inspector grips the same, it is desirable to extend the gripping portion 32 so as to cover the outside of the attaching portion 31. Such is likely applied to other embodiments below.

Further, as shown in FIG. 1, the motive power transmission wire 23 is formed by including an inner wire 42 passed through a flexible cylinder 41. The cylinder 41 is formed by winding, for example, a steel wire in spiral, and by coating the outer surface thereof with a resin. On the other hand, the inner wire 42 is formed by twisting a plurality of fine steel wires, and in the present embodiment, the inner wire is formed so as to permit transmission of forces in both directions of pushing and pulling.

One end of the cylinder 41 of such motive power transmission wire 23 is secured to the gripping portion 32 of the probe holding member 21. Namely, one end of the cylinder 41 is passed through a through hole 38 formed in a direction parallel to the extending direction of the slide rails 36 and is secured to the gripping portion 32 at both sides of the through hole 38 by fastening members 39 such as nuts. Then, one end of the inner wire 42 is secured to the upper face of the stage 33 by a coupling member 43.

Further, the other end of the cylinder 41 of the motive power-transmission wire 23 is secured to the pressing motive power portion 24. Namely, the pressing motive power portion 24 is constituted by being provided with a motor 52, a feed screw 53 one end of which is coupled with the rotation shaft of the motor 52, a supporting member 54 that supports the other end of the feed screw 53 in free of rotation, a feed nut 55 screwed to the feed screw 53 and a slide rail 56 that restricts rotation of the feed nut 55 as well as to support the same in free of sliding. The supporting member 54 is provided with a through hole 57 formed in parallel in the sliding direction of the feed nut 55, the other end of the cylinder 41 of the motive power transmission wire 23 is passed through the through hole 57 and the cylinder 41 is secured to the supporting member 54 at both sides of the through hole 57 by fastening members 58. The other end of the inner wire 42 of the motive power transmission wire 23 is coupled to the feed nut 55 by a securing metal member 59.

The pressing motive power portion 24 thus constituted is assembled in the pressing drive control portion 22 as shown in FIG. 5. Namely, the motor 62 in the pressing motive power portion 24 is connected to a power source 71 via a power source line 62 as well as connected to an operation control circuit 72 via a control line 63. The operation control circuit 72 is formed by, for example, a microcomputer, takes a pressing operation command input from an operation change over interface 74 and controls the motor 52. Further, the operation control circuit 72 also takes a command with regard to a pressing operation input from a device control interface portion 17 via an externally controlled interface 73 and controls the motor 52.

The pressing operation command input from the operation change over interface 74 includes commands for changing over a pressing condition set in advance corresponding to such as a setting for mammary gland, a setting for thyroid gland and a setting for prostate gland other than commands for pressing start and for pressing stop. The operation control circuit 72 controls the rotating operation of the motor 52 according to the an input pressing operation command to thereby change over such as an amplitude (stroke) in up and down direction of the probe 2, an operation speed (pressing cycle) and a varying waveform (sinusoidal wave, square wave) of the operation speed. Further, the motor 52 may be provided with an encoder for grasping rotating conditions of the motor shaft such as original position thereof.

The operation of the thus constituted embodiment 1 will be explained. First of all, the operation of the automated pressing device 3 according to the present embodiment will be explained. After loading the probe 2 in the probe holding member 21 as shown in FIG. 1, while griping the griping portion 32 by hand, the ultrasonics transmission and reception plane 27 of the transducer portion 26 is pressed on the body surface at an object diagnosis portion of the subject 1. Then, when a pressing start command is input from the operation change over interface 74, a control command is output from the operation control circuit 72 to the motor 52 in the pressing motive power portion 24 according to pressing conditions including such as pressing intensity, pressing stroke and pressing cycle that are determined in advance for every pressing modes. Herein the pressing modes and the pressing conditions are set for every kinds of lesion portions of diagnosis objects, for example, such as mammary gland and thyroid gland. For example, in the case of the inspection such as of a mammary cancer, the pressing stroke is determined in a range of 1~3 mm and the pressing cycle is determined as 2 Hz, and in the case of the inspection of a thyroid gland cancer, the pressing stroke is determined further shorter and the pressing cycle is determined in a range of 4~6 Hz, however, such as ranges of these conditions can be modified according to clinical data obtained herein after.

When a control command is input to the motor 52, the motor 52 and the feed screw 53 are rotated in the direction of an arrow 60 in FIG. 1 and the feed nut 55 screwed with the feed screw 53 is driven to advance or retreat along the slide rail 56 in the direction of an arrow 61 in FIG. 1. Through the advance and retreat of the nut 55 the inner wire 42 advances or retreats in the cylinder 41 and the stage 33 is caused to advance or retreat in the direction of an arrow 37 in FIG. 1 with respect to the griping portion 32. When the position of the griping portion 32 is firmly secured with respect to the subject 1, the probe 2 advances or retreats in the direction of the arrow 37 in FIG. 1 via the pair of catching members 34 formed in the stage 33, and the pressing onto the subject 1 is repeated via the ultrasonics transmission and reception plane 27.

While controlling the pressing applied to the subject 1 by the automated pressing device 3 via the probe 2 in the above manner, ultrasonic beams are irradiated to the subject 1 and the reflection echo signals thereof are received successively by scanning. The frame data acquiring portion 12 repeatedly acquires the reflection echo signals output from the phasing and adding circuit 7 in synchronism with the frame rate and stores the same in a frame memory in the order of time sequence. The displacement measuring portion 13 determines displacement vectors at respective measurement points of the subject 1 using as a unit a pair of frame data having different acquiring timings that are selected and successively output by the frame data acquiring portion 12 and output the displacement frame data to the elasticity information computing portion 14.

The elasticity information computing portion 14 determines distortion frame data of a biological tissue at respective measuring points based on the displacement frame data and further determines elastic modules of the biological tissue at respective measuring points based on the distortion frame data to produce elastic module frame data. When determining the elastic modules, stresses at the respective measuring points are computed by taking measured pressure values from the pressure measuring portion 18 and the elastic modules of the biological tissue are determined in a well known manner. The elastic module frame data are subjected to a variety of imaging processings such as smoothing processing in an elasticity information processing portion 15 and sent out to a color scan converter 16. The color scan converter 16 assigns tone codes for every pixels of the input elastic module frame data according to a color map set in advance to produce a colored elasticity image and causes to display the same on the image display 11 via the change over and adding portion 10. At this moment, the change over and adding portion 10 is input of a tomographic image in black and white output from a black and white scan converter 9 and the colored elasticity image output from the color scan converter 16 in response to a command input from the device control interface portion 17 and changes over such as a function of displaying one of both images through changing over, a function of displaying both images in superposed manner on the image display 11 while rendering one of both images in semitransparent and adding the same to synthesizing both and a function of displaying both images in parallel. Further, although not illustrated, through provision of a cine memory portion that stores image data output from the change over and adding portion 10, past image data can be displayed on the image display 11 by calling the same from the cine memory portion according to a command from the device control interface portion 17.

In this manner, a colored elasticity image of elastic modules that are obtained by applying a cyclic pressing to the subject 1 with the automated pressing device 3 according to the present embodiment is displayed on the image display 11. The inspector observes the colored elasticity image and discriminates portions having large elastic modules by color, and thereby judges benignancy or malignancy of the lesion portion such as cancer. Further, in the above explanation, although the elastic modules are exemplifies as the elasticity information, the present invention is not limited thereto, elasticity information relating to hardness of tissues other than the elastic modules (for example, physical quantity relating to tissue elasticity such as visco-elastic module, displacement and distortion) can be used. Further, when a distortion image based on distortion is used, the pressure measuring portion 18 can be eliminated.

In particular, according to the present embodiment, since the operation for driving the probe 2 in up and down direction by the automated pressing device 3 can be performed automatically and constantly by the pressing drive control portion 22, the pressing (pressure application and reduction thereof) to the tissue of the measuring object can be kept stably in a range of desired pressing conditions. As a result, without being affected by a skilled degree a highly reliable elasticity image can be obtained that meets with an objective evaluation.

Further, according to the present embodiment, since the probe 2 is driven to advance and retreat by the feed screw 53, a fine adjustment of operation speed of the probe 2 can be performed as well as since the magnitude of the stroke is easily altered, the present embodiment can be applied to a variety of diagnosis objects. Further, through adjustment of the rotation speed of the motor 52, the operation cycle can be freely varied.

Further, according to the present embodiment, an advantage that the probe 2 can be detachably attached to the probe holding member 21 without necessitating any special tool. More specifically, through application of such as a screw mechanism and spring mechanism in place of the protuberances 35, the upper and lower faces of the probe 2 are pressed and the probe 2 can be secured to the catching members 34, further, when forming the catching members 34 of the probe holding member 21 by a material, for example, such as plastics, rubber and sponge so as to meet different shapes of the probe 2, the catching members 34 can be secured to the probe 2 by an one-touch. Further, the griping portion 32 can be formed in a common shape regardless to the shape of the probe 2. Thereby, the attachment work of the probe 2 can be performed efficiently.

Further, the power source 71 can be realized either in a form of feeding externally or in a form of using a battery including rechargeable one. Further, when a fine wire having an excellent flexibility is employed as the motive power transmission wire 23, the dragging of the probe 2 and the probe holding member 21 can be facilitated. Further, vibrations due to pushing and pulling operation are hardly transmitted to the probe 2. In this instance, only the root portion of the wire coupling with the probe holding member 21 can be made finely to achieve an excellent flexibility.

Embodiment 2

Figure 6:
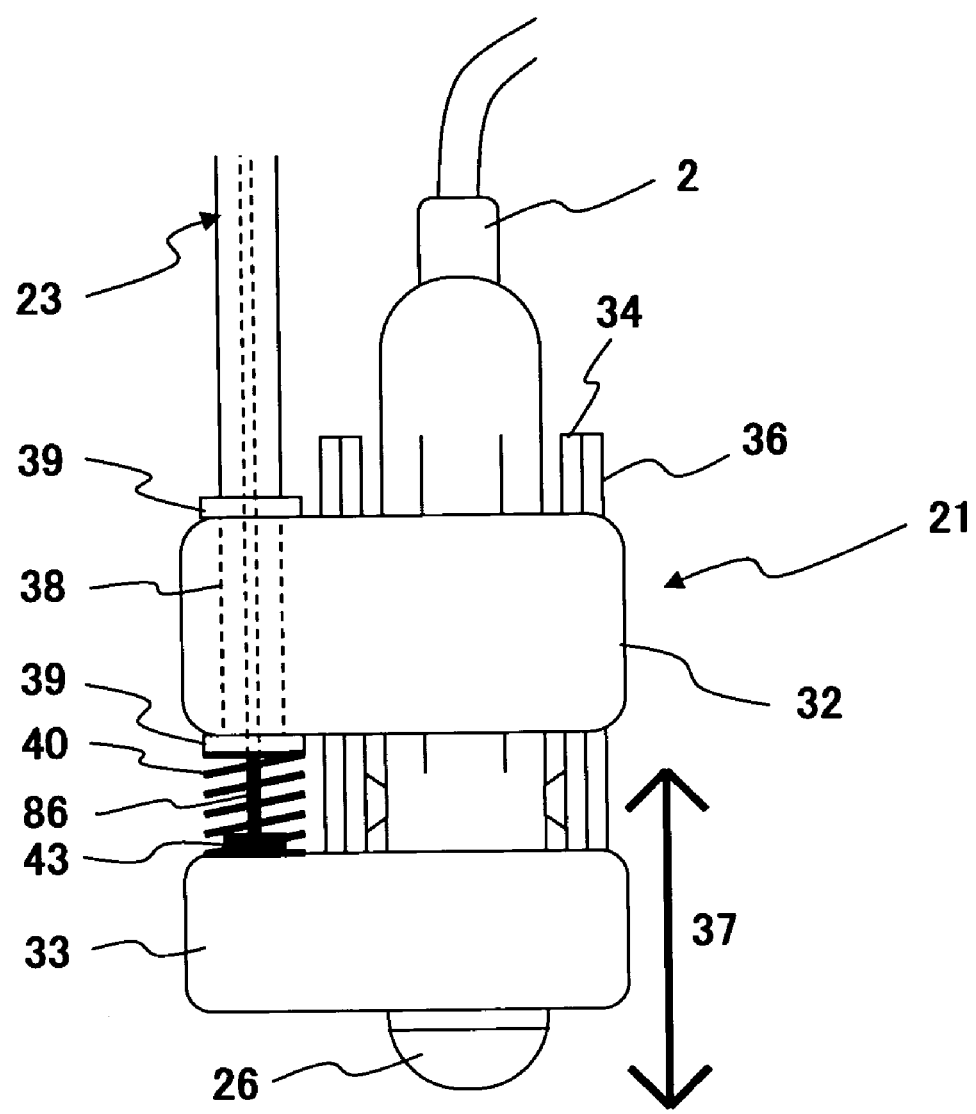
FIG. 6 is a constitutional diagram of an automated pressing device representing an embodiment 2 according to the present invention.

In FIG. 6, the constitution of embodiment 2 of the automated pressing device 3 according to the present invention is shown. A different point of the present embodiment from embodiment 1 is that a flexible inner wire can be used for the motive power transmission wire 23. Namely, since the inner wire 42 in the embodiment 1 is formed of such as a hard steel wire, a force can be transmitted in both directions of pushing and pulling. However, when a flexible or fine steel wire is used, a force can be transmitted in the pulling direction, but a force cannot be transmitted in the pushing direction, because the wire loosens in the pushing direction. In such instance, when the automated pressing device 3 is constituted according to the present embodiment, the pressing operation can be effected. Further, in FIG. 6, parts having the same constitutions as those in embodiment 1 are assigned with the same numerals and the explanation thereof is omitted.

Figure 7:
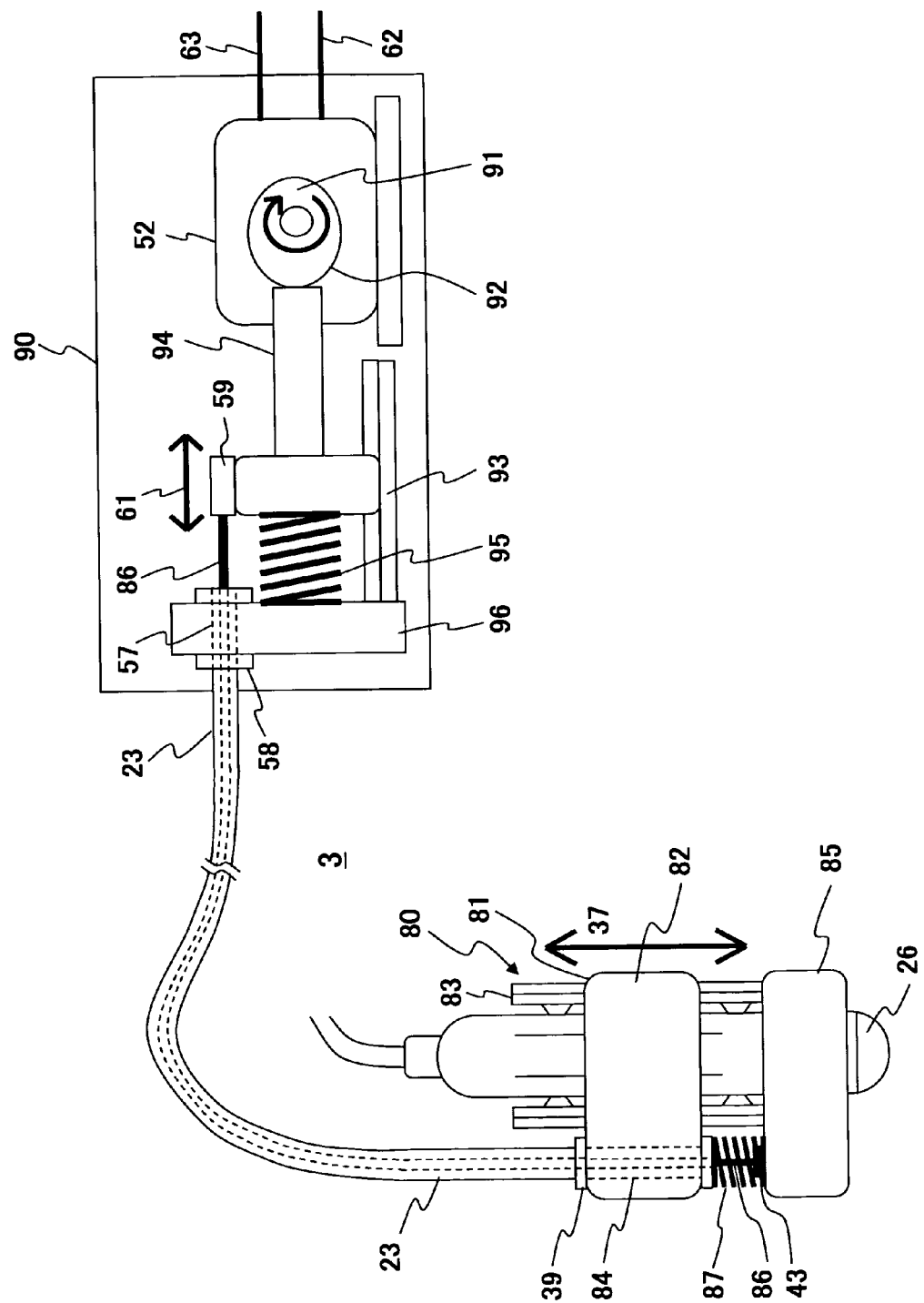
FIG. 7 is a constitutional diagram of an automated pressing device representing an embodiment 3 according to the present invention.

As shown in FIG. 6, the present embodiment is characterized in that between a coupling member 43 on the upper face of the stage 33 and a fastening member 39 on the bottom face of the griping portion 32, a spring 40 energized in the compressing direction is disposed. Namely, since the stage 33 is energized by the spring 40 in the direction moving away from the griping portion 33, the probe 2 is energized in the direction of pressing the subject 1. Further, the pressing motive power portion 24 as shown in FIG. 1 can be applied for the present embodiment as well as a pressing motive power portion 90 as shown in FIG. 7 which will be explained later can likely applied therefor.

Since embodiment 2 is constituted in the above manner, according to the automated pressing device 3 of the present embodiment, like embodiment 1, the inner wire advances or retreats in the cylinder 41 according to the pressing condition in the pressing start command input from the device control interface portion 17 and causes to advance or retreat the stage 33 with respect to the griping portion 32 in the direction of an arrow 37 in FIG. 6. Herein, since an inner wire 86 of the present embodiment uses a flexible or fine steel, a force in the pulling direction can be transmitted, however, a force in the pushing direction cannot be transmitted, because the wire loosens. In the present embodiment, when the inner wire 86 is advanced in the left direction in FIG. 1 to loosen the pulling force, the spring 40 in the probe holding member 21 is expanded and the stage 33 is separated downward in FIG. 6 with respect to the griping portion 32. Thereby, the probe 2 advances downward to perform an operation of applying pressing onto the subject 1 via the ultrasonics transmission and reception plane 27.

Contrary, when the inner wire 86 is pulled in the rightward direction in FIG. 1, the spring 40 in the probe holding member 21 is compressed and the stage 33 is pulled upward in FIG. 6 with respect to the griping portion 32. Thereby, the probe 2 retreats upward and the pressing of the subject 1 can be released.

As has been explained above, according to embodiment 2, even when a flexible inner wire 86 is used, by means of the spring 40 the pressing to the subject 1 is applied via the probe 2 as well as the pressing conditions can be varied.

Further, according to the present embodiment, since the pressing force applied to the subject 1 can be determined by the spring constant of the spring 40, when a spring 40 having a proper spring constant is used, a fear of applying an excess pressing force to the subject 1 can be avoided.

Embodiment 3

Figure 8:
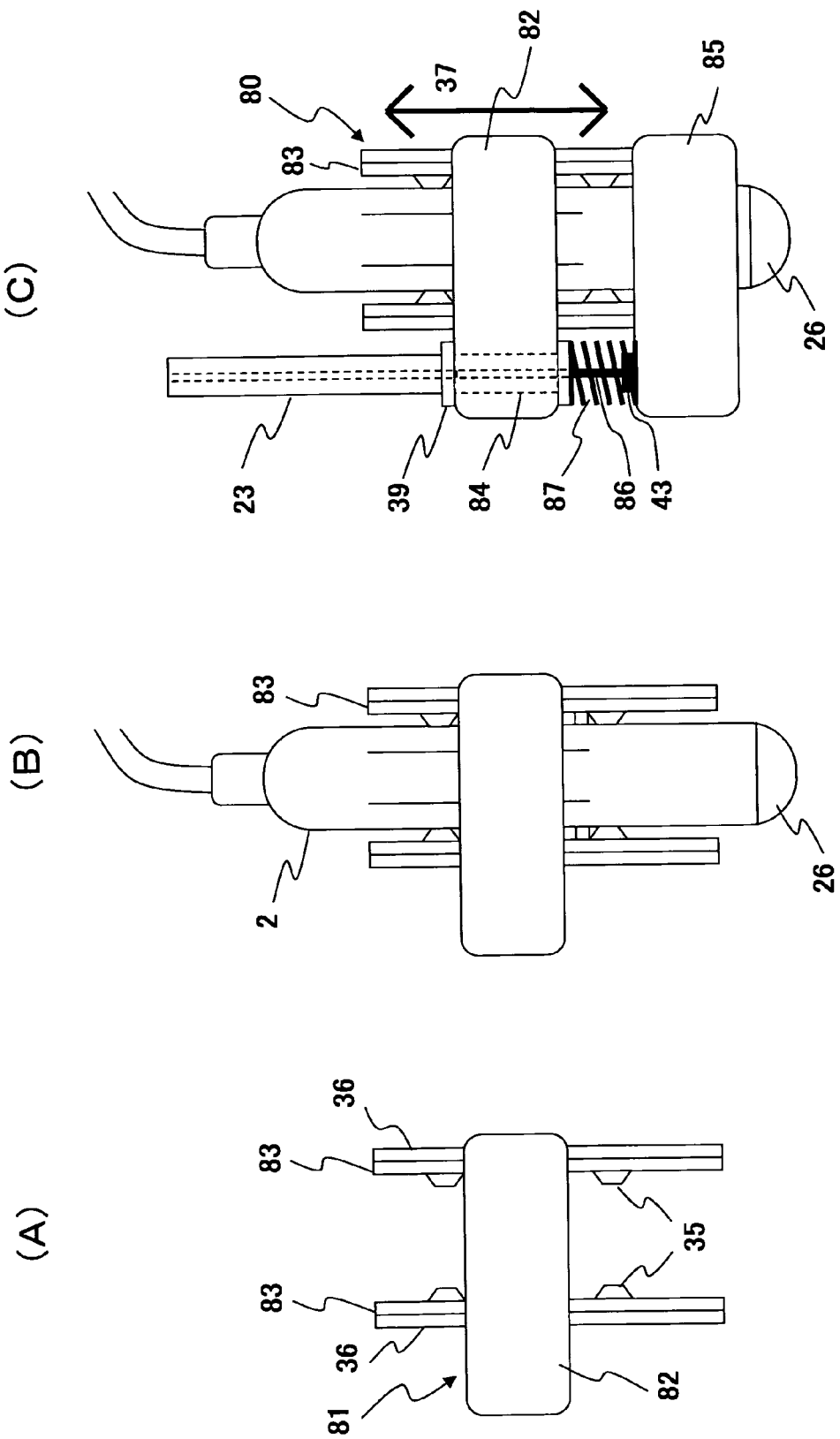
FIG. 8 is a diagram for explaining assembling steps of constitutional parts of the embodiment 3.

In FIGS. 7 and 8, the constitution of embodiment 3 of the automated pressing device 3 according to the present invention is shown. The present embodiment is a modification of embodiment 2 wherein the positional relationship between the stage 33 and the griping portion 32 in the probe holding member 21 in embodiment 2 is inverted. In FIGS. 7 and 8, parts having the same constitutions as those in embodiments 1 and 2 are assigned with the same numerals and the explanation thereof is omitted.

As shown in FIG. 8 (A), in an attaching portion 81 in the probe holding member 80 of the present embodiment, a pair of catching members 83 are respectively formed by standing up the same on both faces of a flat plate stage 82. Further, as shown in FIG. 8 (B), the probe 2 is attached by being caught between the pair of catching members 83. The stage 82 is provided with a hole that permits insertion of the probe 2 like embodiment 1. Further, as shown in FIG. 8 (C), one end of the cylinder 41 for the motive power transmission wire 23 of the present embodiment is inserted in a through hole 84 formed in the stage 82 and is secured to the stage 82 by the fastening member 39 such as a nut.

On one hand, a griping portion 85 is provided with a hole into which the probe 2 can be inserted under a condition of being attached to the pair of catching members 83 and on the inner face of the hole grooves are formed for permitting the slide rails 36 of an attaching portion 81 to slide. However, different from embodiment 1, the griping portion 85 is arranged at the opposite side of the stage 82, namely at the side of the transducer portion 26 of the probe 2. Thereby, the probe 2 is attached so that the ultrasonics transmission and reception plane 27 can be advanced or retreated in the sliding direction of the attaching portion 81 (direction of an arrow 37 in FIGS. 7 and 8 (C)).

Further, one end of an inner wire 86 is secured to the griping portion 85 by the coupling portion 43 and between the fastening member 39 at the bottom face of the stage 82 and the coupling member 43 at the upper face of the griping portion 85 a spring 87 energized in compressing direction is disposed. Namely, by means of the spring 87 the stage 82 is forced to separate with respect to the griping portion 85.

On one hand, as shown in FIG. 7, a pressing motive power portion 90 of the present embodiment is constituted by being provided with a motor 52, an eccentric cam 91 attached to the rotating shaft of the motor 52, an intermediate member 94 that is butted to a cam face 92 of the eccentric cam 91 and is supported in a manner to permit movement in the direction to the axial center of the eccentric cam 91 along a slide rail 93 and a spring 95 serving as an elastic member for pushing the intermediate member 94 to the cam face 92. The other end of the spring 95 is secured to a supporting member 96. The supporting member 96 is provided with a through hole 57 extending in parallel with the sliding direction of the intermediate member 94, an end of the cylinder 41 of the motive power transmission wire 23 is passed through the through hole 57 and is secured to the supporting member 96 at both sides of the through hole 57 by the fastening members 58 such as a nut. An end of the inner wire 86 is coupled to the intermediate member 94 by the fastening metal member 59. Further, the motor 52 is connected to the power source 71 of the pressing drive control portion 22 and the operation control circuit 72 as shown in FIG. 5 via a power source line 62 and a control line 63.

Since the present embodiment is constituted in the above manner, according to the automated pressing device 3 of the present embodiment, as shown in FIG. 7, after loading the probe 2 to the probe holding member 80, while griping the griping portion 85 by hand, the ultrasonics transmission and reception plane 27 is pressed on the body surface in the object diagnosis portion of the subject 1. Then, when a pressing start command is input from the device control interface portion 17, a control command according to the pressing conditions is output from the operation control circuit 72 of the pressing drive control portion 22 to the motor 52. Thereby, the motor 52 is rotated and the eccentric cam 91 is rotated in the arrowed direction. When the eccentric cam 91 is rotated, the intermediate member 94 butted to the cam face 92 is driven to advance or retreat in the direction of the arrow as shown. Through advancing and retreating of the intermediate member 94 the inner wire 86 advances and retreats within the cylinder 41.

However, since the inner wire 86 of the present embodiment uses a flexible steel wire or a fine steel wire, the wire can transmit a force in the pulling direction, but cannot transmit a force in the compressing direction, because the wire loosens. In the case of the present embodiment, when the inner wire 86 is pulled in the right direction in FIG. 7, the force is transmitted via the cylinder 41 of which both ends are secured to compress the spring 87 of the probe holding member 80 and the stage 84 is pulled downward in FIG. 7 toward the griping portion 85. Thereby, the probe 2 advances downward and presses the subject 1 via the ultrasonics transmission and reception plane 27 according to the pressing conditions. On the other hand, when the intermediate member 94 is moved in left direction in FIG. 7 by the eccentric cam 91 to loosen the pulling force to the inner wire 86, the spring 87 in the probe holding member 80 is expanded and the stage 84 is separated in upward in FIG. 7 with respect to the griping portion 85. Thereby, the probe 2 is operated to retreat upward so as to release the pressing applied to the subject 1 via the ultrasonics transmission and reception plane 27.

As has been explained above, according to the present embodiment, even when the flexible inner wire 86 is used, through the rotation of the eccentric cam 91 by the motor 52, the pressing conditions applied to the subject 1 by the automated pressing device 3 via the probe 2 can be varied.

Further, according to the present embodiment, since the pressing force applied to the subject 1 can be determined by the spring constant of the spring 87, when a spring 87 having a proper spring constant is used, a fear of applying an excess pressing force to the subject 1 can be avoided.

Further, according to the present embodiment, through adjustment of rotation speed of the eccentric cam 91, the pressing cycle can be adjusted. However, since the amplitude of the pressing is determined by the amount of eccentricity of the eccentric cam 91, when changing the amplitude of the pressing, the embodiment 1 is preferable.

Further, in place of the eccentric cam 91 of the present embodiment, mechanisms of converting rotating motion to linear motion by a rack and pinion, a crank and a rotatable swash plate as disclosed in patent document 1 can be applied. Concretely, in the mechanism of converting rotating motion to linear motion by a rotatable swash plate, a swash plate cam is secured to the rotating shaft of a motor and an intermediate member butted to a cam face away from the axial rotation center of a swash plate cam is supported so as to permit movement in the axial direction. Further, the intermediate member is pushed to the inclined face via an elastic member and an end of the inner wire is coupled to the intermediate member to constitute the mechanism. Still further, not using the motor, a piston cylinder performing a linear motion can be used.

Embodiment 4

Figure 9:
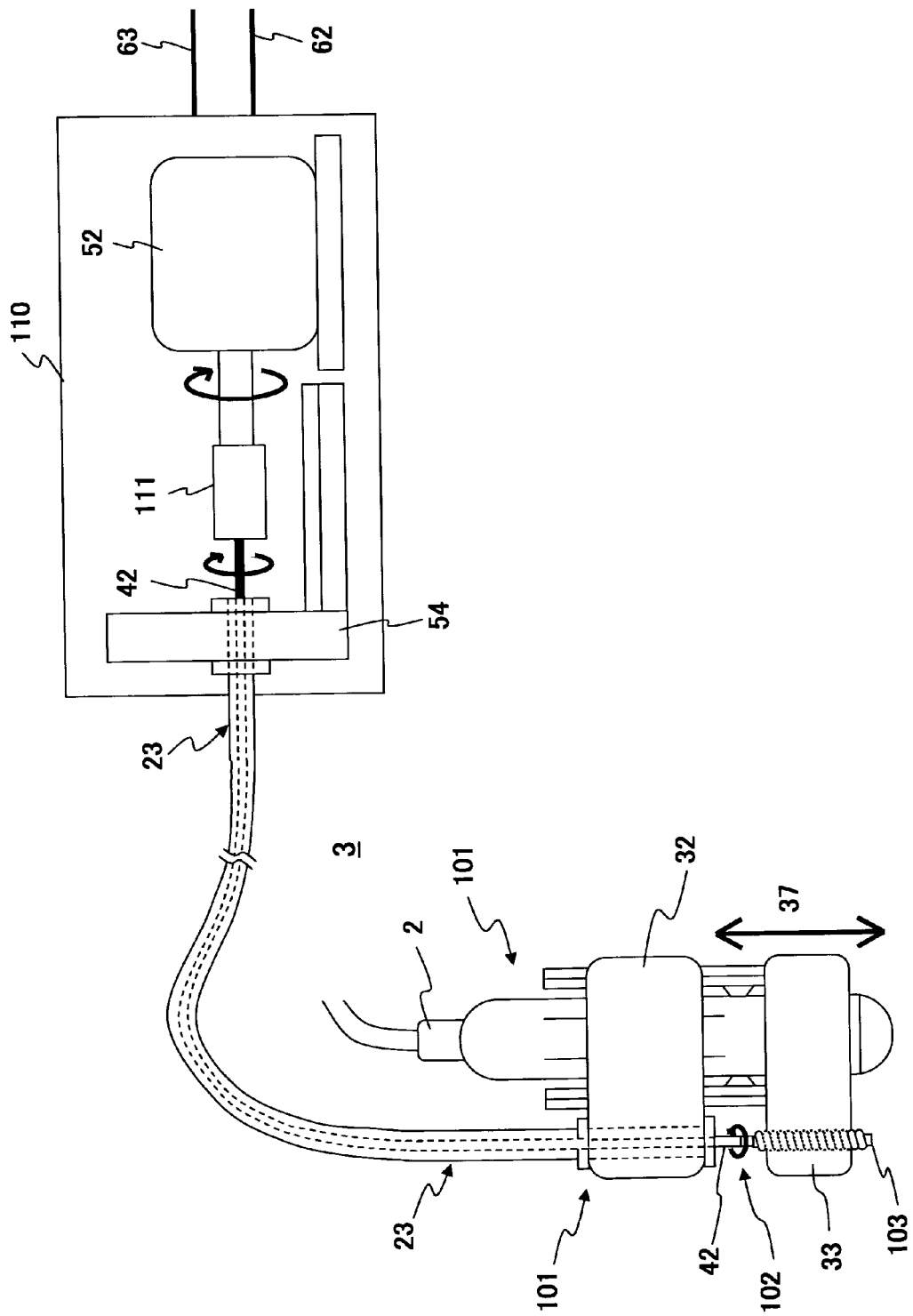
FIG. 9 is a constitutional diagram of an automated pressing device representing an embodiment 4 according to the present invention.
Figure 10:
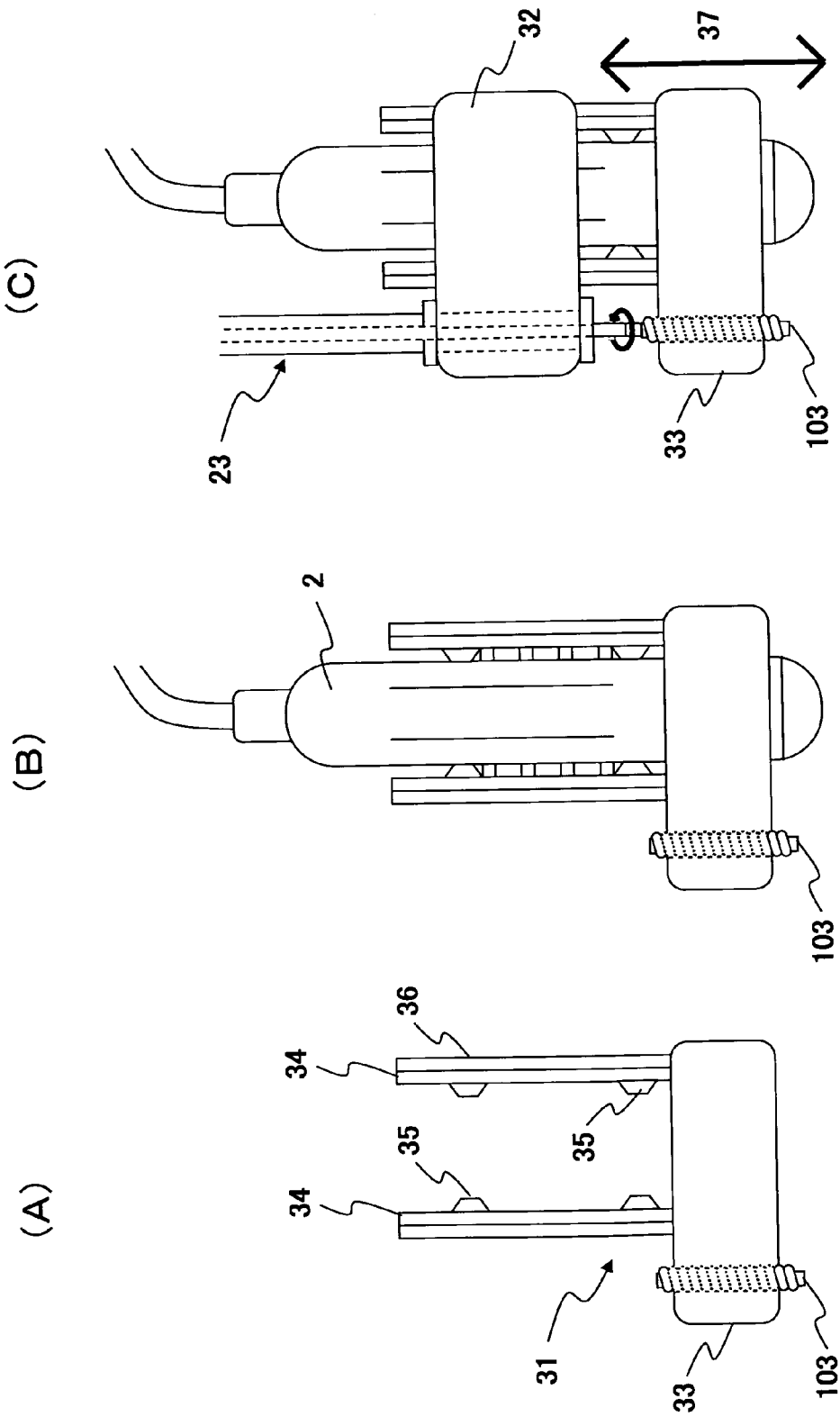
FIG. 10 is a diagram for explaining assembling steps of constitutional parts of the embodiment 4.

In FIGS. 9 and 10, the constitution of embodiment 4 of the automated pressing device 3 according to the present invention is shown. A different point of the present embodiment from embodiments 1~3 is that the motive power is not transmitted through advance or retreat drive of the inner wire 42 in the motive power transmission wire 23, but the motive power is transmitted through rotation thereof.

Namely, as shown in FIG. 9, although an attaching portion 102 in a probe holding member 101 is constituted in the same manner as in embodiment 1 in FIG. 1, a cylindrical nut 103 provided with an inner screw cutting corresponding to the feed nut is buried in the flat plate stage 33. Then a screw provided by screwing in the cylindrical nut 103 is coupled to the inner wire 42. Since the other constitutions are the same as those in embodiment 1, the same reference numerals are assigned thereto and the explanation thereof is omitted.

On the other hand, as shown in FIG. 9, a pressing motive power portion 110 of the present embodiment is constituted by a motor 52 and an inner wire 42 coupled coaxially to the rotating shaft of the motor 52 via a coupling member 111. To the similar constitutional parts as those in embodiments 1 and 2 the same reference numerals are assigned and the explanation thereof is omitted. Further, the motor 52 is connected to the power source 71 of the pressing drive control portion 22 and the operation control circuit 72 as shown in FIG. 5 via a power source line 62 and a control line 63.

Since the present embodiment is constituted in the above manner, according to the present embodiment, when a control command is input to the motor 52, the motor 52 and the inner wire 42 are rotated and the rotating force causes to rotate the screw screwed to the cylindrical nut 103 in the stage 33 via the inner wire 42. Thereby, the top position of the inner wire 42 advances or retreats in the direction of arrow 37 in FIG. 9 with respect to the cylindrical nut 103. Thereby, the interval between the stage 33 and the griping portion 32 varies, thus, when the position of the griping portion 32 is firmly fixed with respect to the subject 1, the probe 2 advances or retreats in the direction of the arrow 37 via the pair of catching members 34 formed at the stage 33 to press the subject 1 via the ultrasonics transmission and reception plane 27 according to the pressing conditions. Since the operations other than the above are the same as those in embodiments 1 and 2, the explanation thereof is omitted.

According to the present embodiment, since the motive power is not transmitted by advancing or retreating the inner wire 42, transmission of vibrations due to advancing and retreating operation of the inner wire 42 to the probe 2 is avoided and a problem of such as back and forth displacement of the measurement cross section with reference to the probe 2 is effectively avoided.

Embodiment 5

Figure 11:
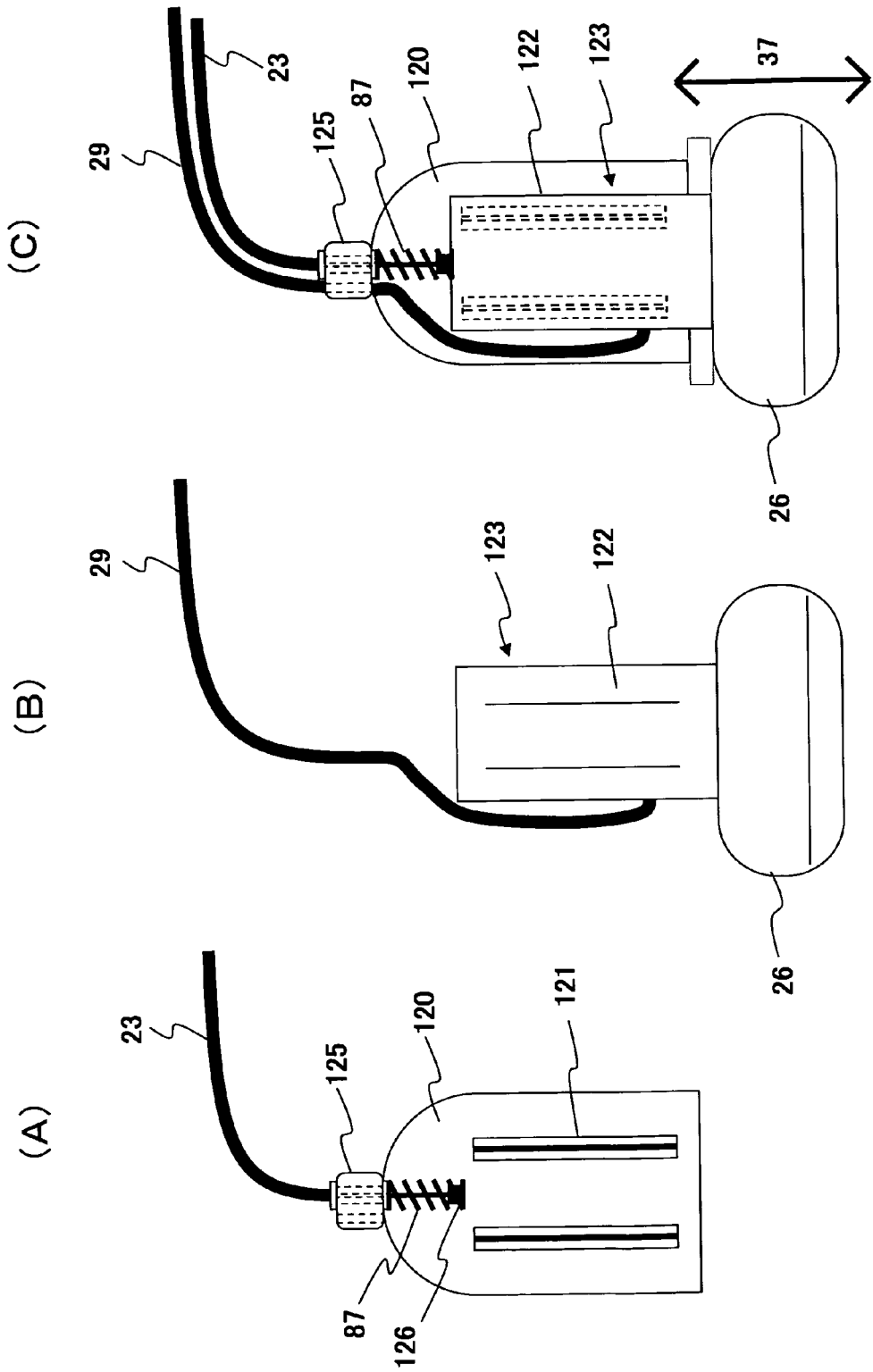
FIG. 11 is a constitutional diagram of an automated pressing device representing an embodiment 5 according to the present invention and is a diagram for explaining assembling steps of constitutional parts of the embodiment 5.

In FIG. 11, the constitution of embodiment 5 of the automated pressing device 3 according to the present invention is shown. A different point of the present embodiment from the other embodiments is that the function of the probe holding member 21 in embodiments 1~4 is incorporated into the probe itself.

Namely, as shown in FIGS. 11 (A) and (B), the probe 2 is divided into a plastic casing 120 constituting the griping portion of the probe 2, the transducer portion 26 and a circuit board portion 122 for driving the transducers. Then, on the inner face of the casing 120, two groove shaped slide rails 121 extending in the pressing direction are formed and grooves slidably engaging with the slide rails 121 are provided on the circuit board portion 122. Then, as shown in FIG. 11 (C), a probe main body portion 123 constituted by the transducer portion 26 and the circuit board portion 122 is attached in the casing 120 along the slide rails 121 so as to permit advancing and retreating with respect thereto.

On one hand, at the top portion of the casing 120, a support and securing portion 125 for the motive power transmission wire 23 and for a probe cable 29 is provided. An end of the cylinder 41 of the motive power transmission wire 23 is passed through a through hole formed in the support and securing portion 125 and secured thereto and an end of the inner wire 42 is coupled to the circuit board portion 122 by a coupling member 126. Further, since the spring 87 is energized in its compressing direction, the coupling member 126 is urged to the direction separating from the support and securing portion 125. On the other hand, the probe cable 29 is led into the casing 120 through a through hole formed in the support and securing portion 125 and is connected to a terminal provided on the circuit board portion 122.

Since the present embodiment is constituted in the above manner, for example, when the inner wire 23 is pulled, the spring 87 is compressed and the transducer portion 26 is pulled up in the direction of the arrow 37 as illustrated via the circuit board portion 122. Further, when the pulling of the inner wire 23 is loosened, the spring 87 expands and the transducer portion 26 is push down in the direction of the arrow 37 as illustrated via the circuit board portion 122. Accordingly, while griping and holding the casing 120 and pressing the ultrasonics transmission and reception plane 27 onto the subject 1, and when the inner wire 23 is advanced or retreated, pressing can be repeatedly applied to the subject 1 via the ultrasonics transmission and reception plane 27. Further, for the present embodiment, either of the pressing motive power portions as shown in FIGS. 1 and 7 can be used.

According to the present embodiment, since the probe portion 26 is attached in the casing 120 constituting the griping portion of the probe 2 so as to permit advancing and retreating thereof and is designed to advance and retreat externally via the motive power transmission wire, a small sized and light weight probe having the pressing function can be realized.

Figure 12:
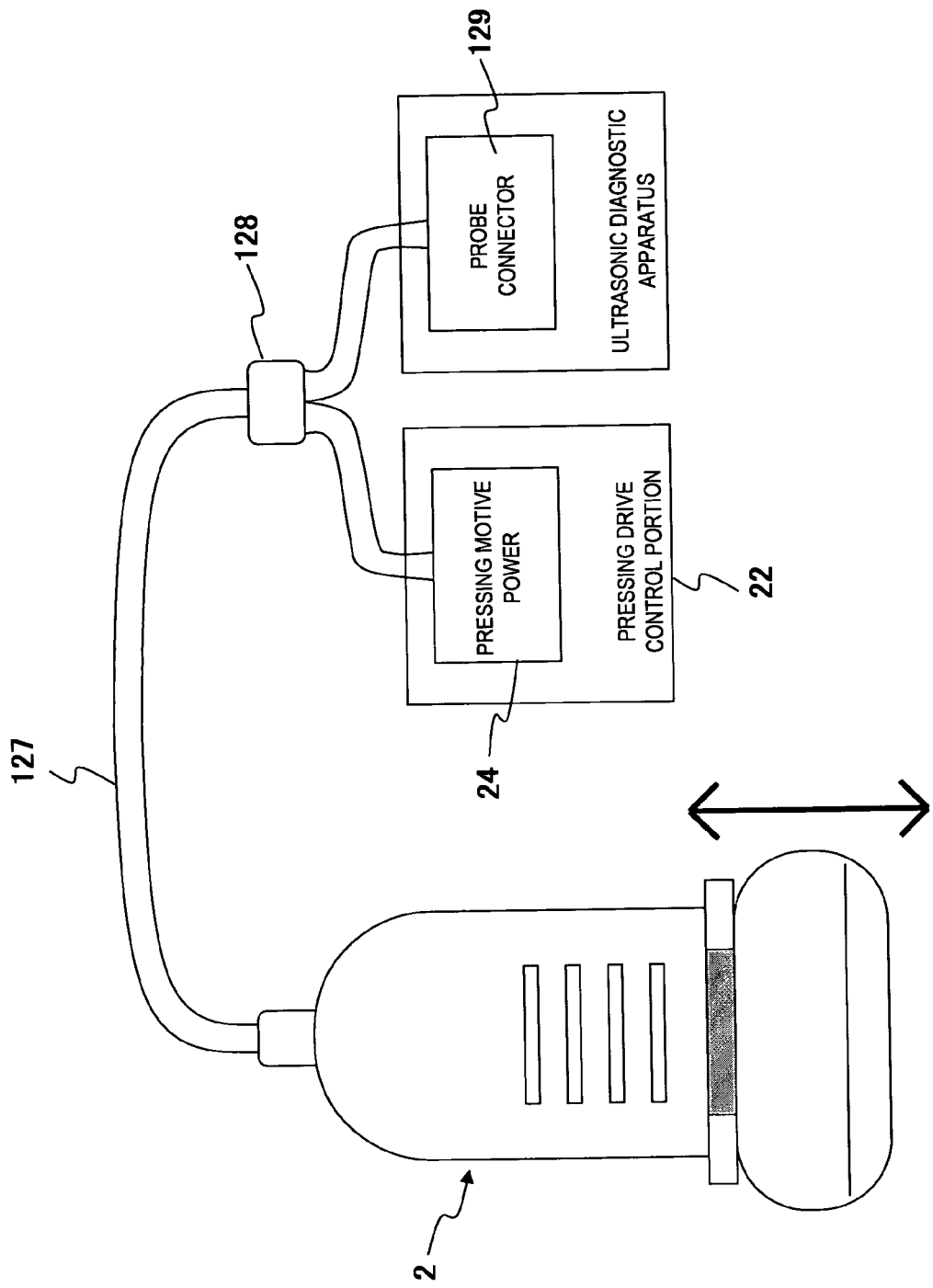
FIG. 12 is a constitutional diagram of a laying of a motive power transmission wire and a probe cable in the embodiment 5.

In the case of the present embodiment, as shown in FIG. 12, the motive power transmission wire 23 and the probe cable 29 can be bundled into a single cable 127. In this instance, through provision of a branching portion 128 at a midway of the cable 127 the motive power transmission wire 23 and the probe cable 29 are separated, the motive power transmission wire 23 is connected to the pressing drive control portion 22 and the probe cable 29 is connected to the transmission circuit 5 and the reception circuit 6 in the ultrasonic diagnosis apparatus via a probe connector 129. The pressing drive control portion 22 can be disposed near or adjacent the probe connector 129 of the ultrasonic diagnosis apparatus. In this instance, the branching portion 128 is preferably disposed near the pressing drive control portion 22. Alternatively, through provision of the branching portion 128 at any midway position of the cable 127, it can be designed to support the pressing drive control portion 22 by the cable 127 itself near the branching portion 128.

According to the present embodiment, since the motive power transmission wire 23 coupled to the probe 2 and the probe cable 29 can be bundled into a single cable 127, the dragging property of the probe 2 is enhanced. Namely, at the time of performing ultrasonic diagnosis and pressing operation, while grasping the probe 2, when the inspector drags the single cable 127 in accordance with the movement of the probe 2, the motive power transmission wire 23 is also dragged in accordance with the movement. Then, when performing ultrasonic diagnosis and pressing operation, a shape such as a curvature of the cable 127 is roughly determined. Accordingly, when performing a pressing operation, since the shape such as a curvature of the motive force transmission wire 23 is rendered in a fixed state, such as a delay of motive power transmission due to the shape of the motive power transmission wire 23 can be minimized and a stable pressing operation can be realized.

Figure 13:
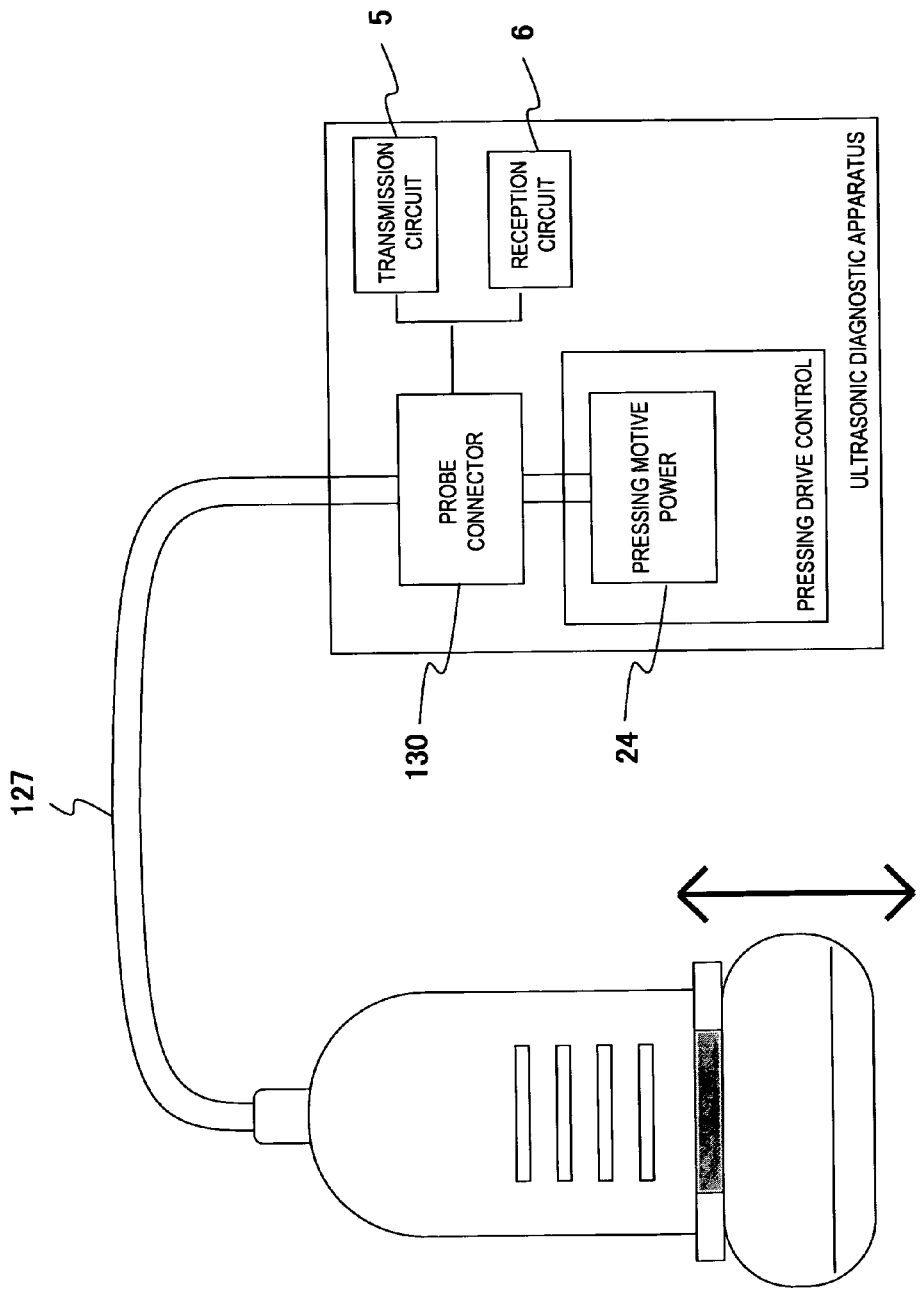
FIG. 13 is a constitutional diagram of another laying of a motive power transmission wire and a probe cable in the embodiment 5.

Further, in the present embodiment as shown in FIG. 12, an example is shown in which the pressing drive control portion 22 is provided separately from the transmission circuit 5 and the reception circuit 6 in the ultrasonic diagnosis apparatus, however, the present invention is not limited thereto and as shown in FIG. 13, the pressing drive control portion 22 can be provided inside the ultrasonic diagnosis apparatus. In this instance, the branching portion 128 and the probe connector 129 can be integrated to form a probe connector 130.

Embodiment 6

In the pressing drive control portion 22 of the respective embodiments above, an example where a command of pressing start or pressing stop is input to the operation control circuit 72 from the operation change over interface 74 is shown as shown in FIG. 5. However, when taking into account of user friendliness for the inspector, it is preferable to provide an input means of such command of pressing start or stop at the probe 2 or the probe holding member 21 to be able to manipulate the same at hand.

Figure 14:
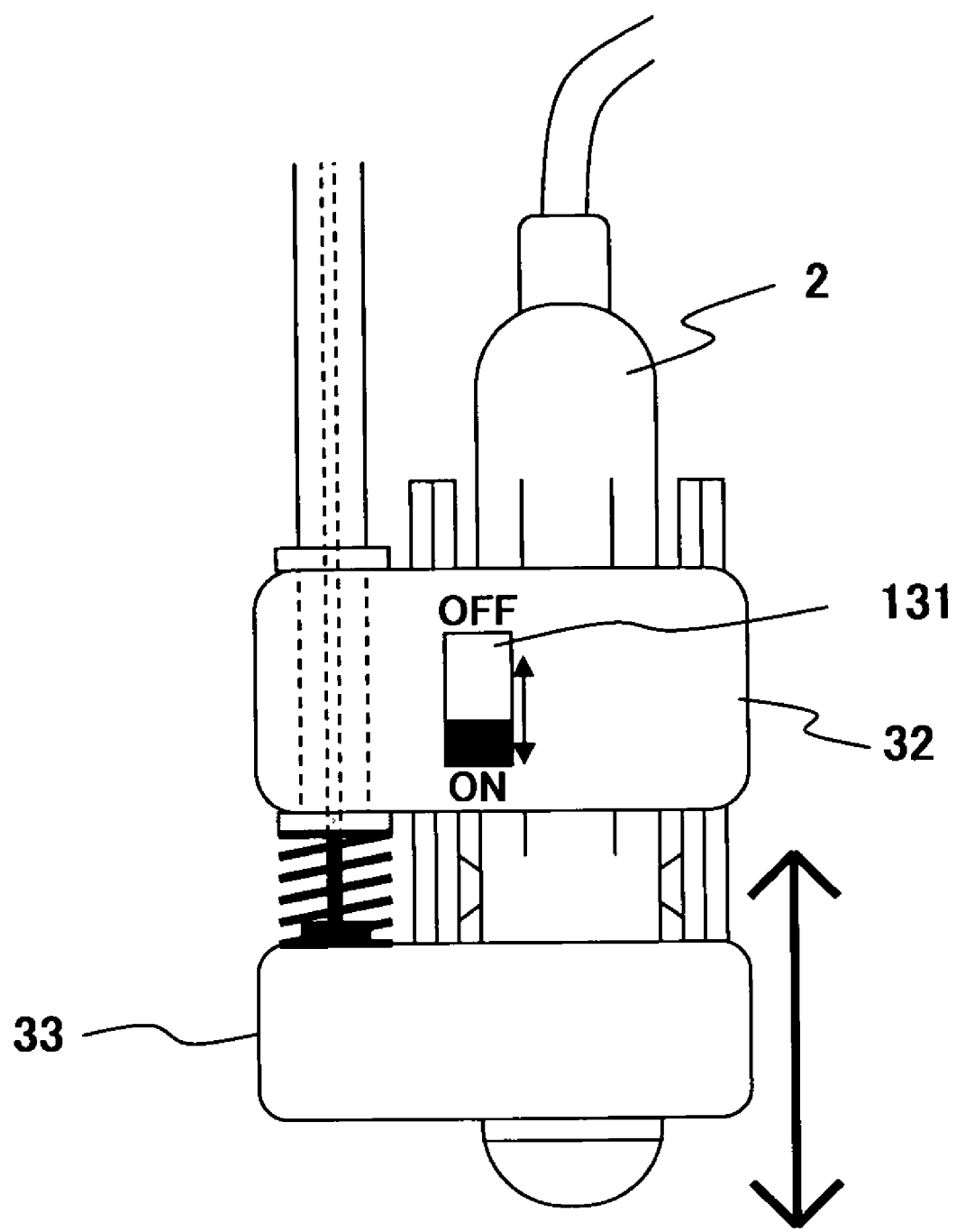
FIG. 14 is a constitutional diagram of a probe holding member in an automated pressing device representing an embodiment 6 according to the present invention.

Accordingly, in the present embodiment, as shown in FIG. 14, a slide type ON/OFF switch 131 representing one embodiment of the operation change over interface 74 is provided at the griping portion 32 and is connected to the operation control circuit 72 in the pressing drive control portion 22 via a control line or wireless communication to input a command of pressing start or stop. Further, other than the ON/OFF switch 131, input means such as a rotary button and a touch panel such as of liquid crystal can be used. Further, a function can be added which permits displaying already set operating conditions until now on a liquid display screen at the operation change over interface circuit 74 to confirm the same.

Embodiment 7

In the pressing drive control portion 22 of the respective embodiments above, an example where the operation control circuit 72 is connected to the operation change over interface 74 via a control line is shown as shown in FIG. 5. Further, an example is shown where the operation control circuit 72 is connected to the device control interface 17 via the external control interface 73 through control a line. However, these can be connected through wireless such as of infrared rays.

However, the present invention is not limited thereto, the present invention can be modified in such a manner that the operation control circuit 72 is incorporated into the device control interface 17 so as to directly control the pressing motive power portion 24 from the device control interface 17. In this instance, the device control interface 17 and the pressing motive power portion 24 can be connected by a control line or wireless of such as infrared rays.

Further, pressing conditions provided to the operation control circuit 72 can be displayed on the image display 11 in the ultrasonic diagnosis apparatus as well as can be recorded on an elasticity image.

Embodiment 8

Further, by detecting actual pressing conditions based on the movement of the pressing motive power portion 24 and stage 33, the detected conditions can be displayed on the image display 11 as well as recorded on an elasticity image. For example, the separation interval between the griping portion 32 and the stage 33 in FIG. 1 is measured by an optical sensor such as of infrared rays and actual pressing conditions are detected based on the positional variation of the stage 33 with respect to the griping portion 32.

According to the present embodiment, when the stage 33 is not driven according to a designated operation due to such as elongation of such as the inner wire 42 or deflection of such as the inner wire 42 during the measurement, the actual operating conditions can be confirmed by directly detecting the position of the stage 33 and thereby the operation can be adjusted so as to realize the desired operation setting.

Embodiment 9

Figure 15:
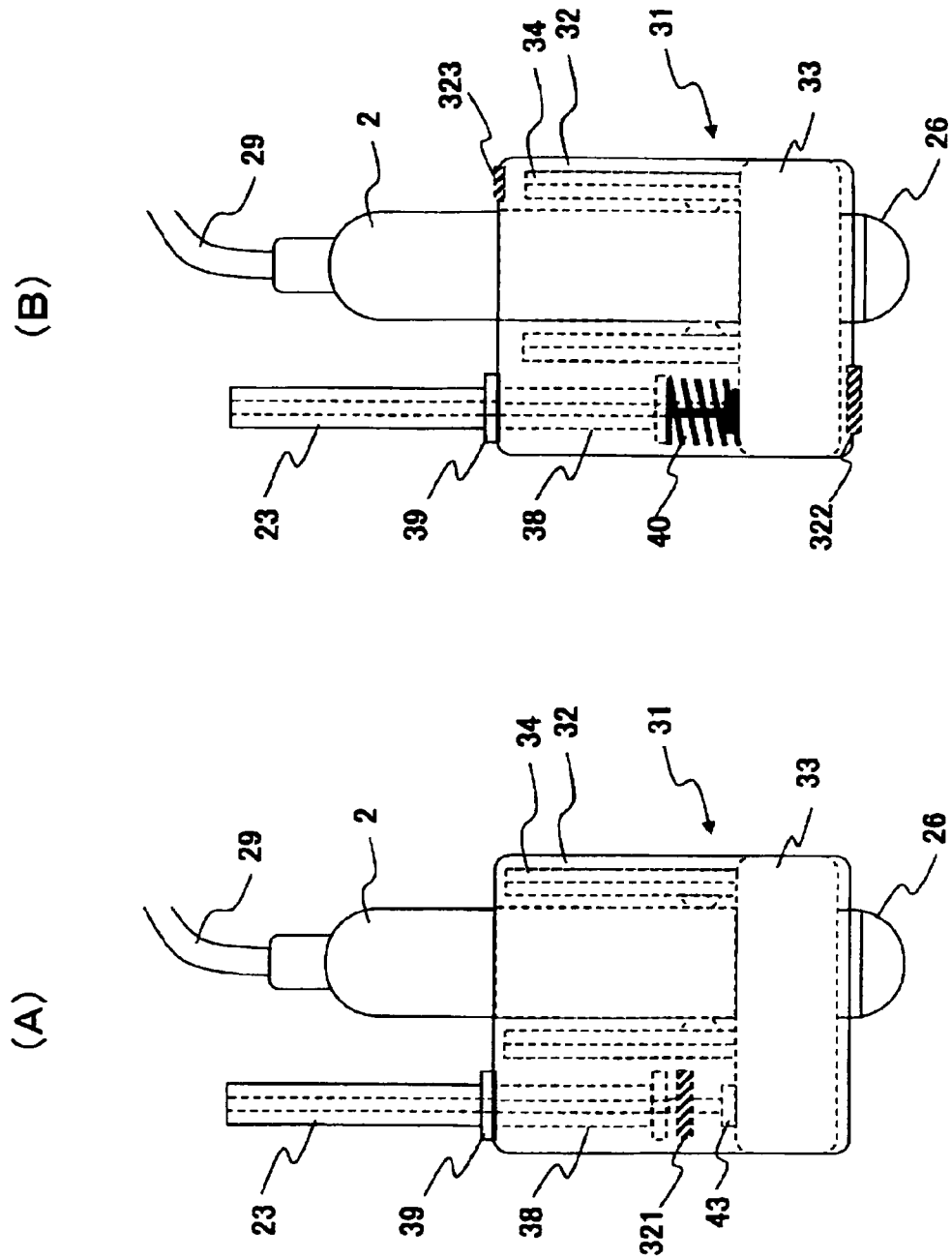
FIG. 15 is a constitutional diagram of an automated pressing device representing an embodiment 9 according to the present invention.

As shown in FIGS. 15 (A) and (B), the griping portion 32 can be formed large in comparison with those in the other embodiments so that the griping portion 32 contains the stage portion 33 and internal parts such as the catching members 34. When an operator contacts the probe 2 to the subject 1 while griping the griping portion 32, the pressing to the subject 1 can be performed further safely. Further, in FIG. 15, the parts having the same constitutions as those in embodiments 1 and 2 are designated by the same reference numerals and the explanation thereof is omitted.

Further, as shown in FIG. 15 (A), in order not to protrude the stage portion 33 and the internal parts such as the catching members 34 from the griping portion 32, a stopper 321 is provided at the top end of the motive power transmission wire 23 to suppress the movement by the motive power transmission wire 23. For example, when the motive power transmission wire 23 is pulled upward, the stopper 321 hits to the end portion of the through hole 38 and the movement of the motive power transmission wire 23 can be suppressed.

Further, as shown in FIG. 15 (B), in order not to protrude the stage 33 from the bottom side of the griping portion 32, a stopper 322 is provided at the bottom end of the griping portion 32. When pushing the motive power transmission wire 23 downward, the stage portion 33 hits the stopper 322 and the movement of the stage portion 33 can be suppressed. Further, in order not to protrude the catching members 34 from the upper side of the griping portion 32, a stopper 322 is provided at the top end of the griping portion 32. When the motive power transmission wire 23 is pulled upward, the catching members 34 hit the stopper 322 and the movement of the catching members 34 is suppressed. When the present embodiment is applied, a possible catching of fingers of an operator between the stage portion 33 and the catching members 34 can be prevented.

The invention claimed is:

1. An automated pressing device comprising:
   a probe;
   a drive portion disposed away from the probe and configured to advance and retreat the probe in the direction of ultrasonic transmission and reception;
   a motive power transmission portion configured to transmit a motive power of the drive portion to the probe; and
   a pressing device including:
      a first member configured to detachably hold the probe and further configured as an attaching portion coupled to the motive power transmission portion, and
      a second member configured to hold the first member so as to permit advancing and retreating of the probe in the direction of ultrasonic transmission and reception, and further configured as a gripping portion for allowing movement of the probe in 3 dimensional space,
   wherein one end of the motive power transmission portion is coupled to the drive portion and a second end of the motive power transmission portion is coupled to the first member via a coupling member, and
   wherein the first member is configured to be advanced and retreated with respect to the second member.

2. An automated pressing device according to claim 1, wherein the motive power transmission portion includes a cylinder having one end secured to the second member and a second end secured to the drive portion, and wherein the coupling member which is inserted through the cylinder and one end thereof is coupled to the first member.

3. An automated pressing device according to claim 2, wherein the coupling member in the motive power transmission portion is a motive power transmission wire of an inner wire.

4. An automated pressing device according to claim 1, wherein an elastic member is disposed between the first member and the second member to be energized in the direction separating both members.

5. An automated pressing device according to claim 3, wherein the second member is a casing for forming a gripping portion of the probe, and further comprising:
   slide rails formed on inner faces of the casing,
   sliding members accommodated in the casing so as to permit sliding along the slide rails, and
   a transducer portion secured to the sliding members while protruding the ultrasonic transmission and reception plane of the probe from the casing and an elastic member energized in the direction of advancing the transducer portion from the casing along the slide rails,
   wherein the cylinder is of flexible and is secured to one end of the casing, and
   wherein the inner wire in the motive power transmission wire is inserted through the cylinder and one end thereof is coupled to the sliding members and the second end of the cylinder in the motive power transmission wire is secured to the drive portion so as to advance or retreat the other end of the inner wire.

6. An automated pressing device according to any one of claims 3 through 5, wherein the drive portion is provided with a feed screw coupled to a rotary shaft of a motor and rotatably supported and a feed nut screwed to the feed screw and the other end of the inner wire is coupled to the feed nut.

7. An automated pressing device according to any one of claims 3 through 5, wherein the drive portion includes an eccentric cam secured to a rotary shaft of a motor, an intermediate member abutted to a cam face of the eccentric cam and movably supported in the direction of the center axis of the eccentric cam and a spring member pushing the intermediate member toward the cam face, and a second end of the inner wire is coupled to the intermediate member.

8. An automated pressing device according to any one of claims 3 through 5, wherein the drive portion includes a swash plate cam secured to a rotary shaft of a motor, an intermediate member abutted to a cam face away from the center of rotary axis of the swash plate cam and movably supported in the direction of the axis thereof and a spring member pushing the intermediate member toward the cam face, and the second end of the inner wire is coupled to the intermediate member.

9. An automated pressing device according to claim 1, wherein the first member includes a screw disposed along the direction of movement toward or away of the second member and the first member and screwed to the first member, the motive power transmission portion is a motive power transmission wire and includes a flexible cylinder of which one end is secured to the second member and an inner wire which is passed through the cylinder and of which one end is coupled to the screw, the second end of the cylinder in the motive power transmission wire is secured to the drive portion and the second end of the inner wire is coupled to the drive portion to thereby rotatably drive the inner wire.

10. An automated pressing device according to claim 4, wherein the drive portion is configured to advance and retreat the probe attached to the first member by periodically pulling or releasing the pulling force via the inner wire in the motive power transmission wire.

11. An automated pressing device according to claim 10, wherein when the pulling force by the drive portion via the inner wire in the motive power transmission wire is released, the probe attached to the first member is advanced by the spring force of the elastic member.

12. An automated pressing device according to claim 4, wherein the first member includes at the inner side thereof at least one pair of catching members which permit detachable loading of the probe and includes at the outside thereof a sliding member which permits sliding of the second member.

13. An automated pressing device according to claim 12, wherein the second member is formed so as to cover at least a part of the outer circumference of the first member.

14. An automated pressing device according to claim 12, wherein the shape of the pair of catching members in the first member is formed in a dedicated manner so as to match the shapes of a variety of probes to be attached and the sliding member formed at the outside of the first member is configured to be engagable with the second member formed in common.

15. An automated pressing device according to claim 1, wherein the second member is configured to surround the first member as well as the first member, and includes a stopper that prevents the second member from protruding from the first member.

16. An automated pressing device according to claim 1, wherein the second member or the casing of the probe is provided with an input means that inputs an operation command to the drive portion.

17. An ultrasonic diagnosis apparatus comprising:
 an automated pressing device according to any one of claims 1 through 16;
 and further comprising:
 a transmission circuit for outputting ultrasonic pulses to drive the probe;
 a reception circuit for receiving reflected echo signals;
 a transmission/reception control circuit for controlling the transmission circuit and the reception circuit;
 a scan converter for generating tomographic image data based on the reflected echo signals; and
 a display unit for displaying a tomographic image representative of the tomographic image data.

* * * * *